US 8,410,064 B2
Apr. 2, 2013

(12) United States Patent
Radominska-Pandya et al.

(10) Patent No.: US 8,410,064 B2
(45) Date of Patent: Apr. 2, 2013

(54) CLASSICAL CANNABINOID METABOLITES AND METHODS OF USE THEREOF

(75) Inventors: Anna Radominska-Pandya, Little Rock, AR (US); Grover Miller, Little Rock, AR (US); Jeffery Moran, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 241 days.

(21) Appl. No.: 12/862,501

(22) Filed: Aug. 24, 2010

(65) Prior Publication Data

US 2011/0046081 A1    Feb. 24, 2011

Related U.S. Application Data

(60) Provisional application No. 61/236,298, filed on Aug. 24, 2009.

(51) Int. Cl.
*A01N 43/04*    (2006.01)
*A61K 31/70*    (2006.01)

(52) U.S. Cl. ............... 514/27; 514/23; 514/25; 536/124; 536/127

(58) Field of Classification Search ........................ None
See application file for complete search history.

(56) References Cited

U.S. PATENT DOCUMENTS

| | | | |
|---|---|---|---|
| 4,241,046 | A | 12/1980 | Papahadjopoulos et al. |
| 4,394,448 | A | 7/1983 | Szoka, Jr. et al. |
| 4,529,561 | A | 7/1985 | Hunt et al. |
| 4,755,388 | A | 7/1988 | Heath et al. |
| 4,828,837 | A | 5/1989 | Uster et al. |
| 4,925,661 | A | 5/1990 | Huang |
| 4,954,345 | A | 9/1990 | Muller |
| 4,957,735 | A | 9/1990 | Huang |
| 5,043,164 | A | 8/1991 | Huang et al. |
| 5,064,655 | A | 11/1991 | Uster et al. |
| 5,077,211 | A | 12/1991 | Yarosh |
| 5,264,618 | A | 11/1993 | Felgner et al. |
| 6,136,839 | A | 10/2000 | Isakson et al. |
| 2002/0198167 | A1 | 12/2002 | Czernik et al. |
| 2003/0215462 | A1 | 11/2003 | Wacher et al. |
| 2005/0074745 | A1 | 4/2005 | Clayton et al. |
| 2006/0153808 | A1 | 7/2006 | Cristofanilli et al. |
| 2006/0275371 | A1 | 12/2006 | Dai et al. |
| 2007/0259894 | A1 | 11/2007 | Kassahun |
| 2010/0226856 | A1 | 9/2010 | Vitaliano et al. |
| 2010/0273203 | A1 | 10/2010 | Miller et al. |
| 2011/0236495 | A1 | 9/2011 | Radominska-Pandya et al. |
| 2012/0165280 | A1 | 6/2012 | Mayeux et al. |
| 2012/0165281 | A1 | 6/2012 | Radominska-Pandya et al. |
| 2012/0184536 | A1 | 7/2012 | Radominska-Pandya |

FOREIGN PATENT DOCUMENTS

| | | | |
|---|---|---|---|
| WO | 2011026112 | A1 | 8/2010 |
| WO | 2011017456 | A2 | 2/2011 |

OTHER PUBLICATIONS

Wienmann et al. Forensic Science International (2000), vol. 113, pp. 381-387.*
Naef et al. Pain (2003), vol. 105, pp. 79-88.*
Gustafson et al. Journal of Chromatography B (2003), vol. 798, pp. 145-154.*
Lyle et al. Biomedical Mass Spectrometry (1977), vol. 4, pp. 190-196.*
Au, N. et al., "Pharmacogenomics of 4-hydroxycoumarin anticoagulants," Drug Metab. Rev., 2008, pp. 355-375, vol. 40.
Banfield, C. et al., "Phenylbutazone-Warfarin Interaction in Man: Further Stereochemical and Metabolic Considerations," Br. J. Clin. Pharmac. (1983) pp. 669-675, vol. 16.
Barua, A. et al., "Chemical synthesis and growth-promoting activity of all-trans-retinyl β-D-glucuronide," Biochem. J., (1987), pp. 231-234, vol. 244.
Blaner, et al., Retinol and retinoic acid metabolism: The Retinoids. Biology, Chemistry, and Medicine (Sporn MB. Roberts AB and Goodman DS eds). (1994), pp. 229-255. Raven Press, New York.
Medication Guide for Coumadin Tablets (Warfarin Sodium Tablets, USP) distributed by Bristol-Myers Squibb, Jan. 2009, 6 pages.
Brotchie, J., "CBI cannabinoid receptor signaling in Parkinson's disease. Current Opinion in Pharmacology," Feb. 2003, pp. 54-61, vol. 3, No. 1 (abstract only).
Court, M. et al., "Evaluation of 3'-azido-3'-deoxylhymidine, morphine, and codeine as probe substrates for UDP-glucuronosyltransferase 2B7 (UGT2B7) in human liver microsomes: specificity and influence of the UGT2B7*2 polymorphism," Drug Metab. Dispos., 2003, pp. 1125-1133, vol. 31, No. 9.
Chan, E. et al., "Disposition of warfarin enantiomers and metabolites in patients during multiple dosing with rac-warfarin," Br. J. Clin. Pharmac., 1994, pp. 563-569, vol. 37.
Cooper, G. et al., "A genome-wide scan for common genetic variants with a large influence on warfarin maintenance dose," Blood, Aug. 15, 2008, pp. 1022-1027, vol. 112, No. 4.
Dettmer, K. et al., "Mass-Spectrometry-Based Metabolomics," Mass. Spectrom. Rev., 2007, pp. 51-78, vol. 26, No. 1 (with 19 pages of author manuscript).
Eble, J. et al., "A comparison of the isomers of warfarin," Biochem. Pharmacol., 1966, pp. 1003-1006, vol. 15, Pergamon Press Ltd., Great Britain.
Galiegue, S. et al., "Expression of central and peripheral cannabinoid receptors in human immune tissues and leukocyte subpopulations." Eur. J. Biochem., 1995, pp. 54-61, vol. 232.
Gallup, J. et al., "Effects of retinoid betaglucuronides and N-retinoyl amities on the differentiation of HL-60 cells in vitro," Proc. Soc. Exp. Biol. Med., Dec. 1987, pp. 269-274, vol. 186, No. 3 (abstract only).
Gebauer, M., "Synthesis and structure-activity relationships of novel warfarin derivatives," Bioorg. & Med. Chem., 2007, pp. 2414-2420, vol. 15.
Grancharov, K. et al., "Natural and synthetic inhibitors of UDP-glucuronosyltransferase," Pharmacology & Therapeutics, 2001, pp. 171-186, vol. 89, No. 2.

(Continued)

*Primary Examiner* — Patrick Lewis
(74) *Attorney, Agent, or Firm* — Polsinelli Shughart PC

(57) ABSTRACT

The present invention encompasses classical cannabinoid metabolites and uses thereof.

5 Claims, 16 Drawing Sheets

OTHER PUBLICATIONS

Haining, R. et al., "Allelic Variants of Human Cytochrome P450 2C9: Baculovirus-Mediated Expression, Purification, Structural Characterization, Substrate Stereoselectivity and Prochiral Selectivity of the Wild-Type and I359L Mutant Forms," Arch. Biochem. Biophys., Sep. 15, 1996, pp. 447-458,vol. 333, No. 2.

Hirsh, J. et al., "Oral Anticoagulants: Mechanism of Action, Clinical Effectiveness, and Optimal Therapeutic Range," Chest, 2001, pp. 8S-21S, vol. 119.

Holbrook, A. et al., "Systematic Overview of Warfarin and Its Drug and Food Interactions," Arch. Intern. Med., May 23, 2005, pp. 1095-1106, vol. 165.

Howlett, A., "Pharmacology of cannabinoid receptors," Annu. Rev. Pharmacol. Toxicol., 1995, pp. 607-634, vol. 35.

Hyland, R. et al., "In vitro and in vivo glucuronidation of midazolam in humans," Br. J. Clin. Pharmacol., Apr. 2009, 445-54, vol. 67, No. 4.

International Search Report and Written Opinion for PCT Application No. PCT/US10/47340, Oct. 26, 2010, 7 pages.

Iversen, L. et al. "Cannabinoids: a real prospect for pain relief," Current Opinion in Pharmacology, 2002, pp. 50-55 , vol. 2.

Janick-Buckner, D. et al., "Induction of HL-60 cell differentiation by water-soluble and nitrogen-containing conjugates of retinoic acid and retinol," FASEB J., Mar. 1991, pp. 320-325, vol. 5.

Jansing, R. et al., "Phase II Metabolism of Warfarin in Primary Culture of Adult Rat Hepatocytes," Mol. Pharmacol., 1991, pp. 209-215, vol. 41.

Kaminsky, L. et al., "Correlation of Human Cytochrome P4502C Substrate Specificities with Primary Structure: Warfarin as Probe," Mol. Pharmacol., 1992, pp. 234-239, vol. 43.

Kaminsky, L. et al., "Human P450 Metabolism of Warfarin," Pharmacol. Ther., 1997, pp. 67-74, vol. 73, No. 1.

Klein, T. et al., "The cannabinoid system and immune modulation," Journal of Leukocyte Biology, Oct. 2003, pp. 486-496, vol. 74.

Kurkela, M. et al., "Expression and characterization of recombinant human UDPglucuronosyltransferases (UGTs). UGT I A9 is more resistant to detergent inhibition than other UGTs and was purified as an active dimeric enzyme," J. Biol. Chem., Feb. 7, 2003, pp. 3536-3544, vol. 278, No. 6.

Kuuranne, T. et al., "Glucuronidation of anabolic androgenic steroids by recombinant human LDP glucuronosyltransferases," Drug Metab. Dispos., 2003, pp. 1117-1124, vol. 31, No. 9.

Lee, J. et al., "Metabolism of Vitamin K and Vitamin K 2,3-Epoxide via Interaction with a Common Disulfide," Biochemistry, Mar. 27, 1984, pp. 2246-2252, vol. 23, No. 10.

Lesko, L., "The Critical Path of Warfarin Dosing: Finding an Optimal Dosing Strategy Using Pharmacogenetics," Clin. Pharmacol. Ther., Sep. 2008, pp. 301-303, vol. 84, No. 3.

Limdi, N. et al., "Kidney Function Influences Warfarin Responsiveness and Hemorrhagic Complications," J. Am. Soc. Nephrol., 2009, pp. 912-921, vol. 20.

Little, J. et al., "Glucuronidation of oxidized fatty acids and prostaglandins B1 and E2 by human hepatic and recombinant LIDP-alucuronosyltransferases," J. Lipid Res., 2004, pp. 1694-1703, vol. 45.

Matsuda, L. et al., "Structure of a cannabinoid receptor and functional expression of the cloned cDNA," Nature, Aug. 9, 1990, pp. 561-564, vol. 346.

Miller, G. et al., "Assessing Cytochrome P450 and UDP-Glucuronosyltransferase Contributions to Warfarin Metabolism in Humans," Chem. Res. Toxicol., Jul. 2009, 14 pages, vol. 22, No. 7.

Miller, G. et al., "Identification of Hydroxywarfarin Binding Site in Human UDP Glucuronosyltransferase 1A10: Phenylalanine90 is Crucial for Glucuronidation of 6- and 7-Hydroxywarfarin but Not 8-Hydroxywarfarin," Drug Metabolism and Disposition, 2008, pp. 2211-2218, vol. 36, No. 11.

Munro, S. et al., "Molecular characterization of a peripheral receptor for cannabinoids," Nature, Sep. 2, 1993, pp. 61-65, vol. 365, No. 6441.

Ngui, J. et al., "In Vitro Stimulation of Warfarin Metabolism by Quinidine: Increases in the Formation of 4'- and 10-hydroxywarfarin," Drug Metabolism and Disposition, 2001, pp. 877-886, vol. 29, No. 6.

O'Reilly, R., "Interaction of the Anticoagulant Drug Warfarin and Its Metabolites with Human Plasma Albumin," J. Clin. Investigation, 1969, pp. 193-202, vol. 48.

Racz, I. et al., "A critical role for the cannabinoid CB 1 receptors in alcohol dependence and stress-stimulated ethanol drinking," J. Neuroscience, Mar. 15, 2003, pp. 2453-2458, vol. 23, No. 6.

Radominska, A. et al., "Photoaffinity labeling for evaluation of uridinyl analogs as specific inhibitors of rat liver microsomal UDP-glucuronosyltransferases," Biochimica et Biophysica Acta, 1994, pp. 336-345, vol. 1205, No. 2.

Radominska-Pyrek, A. et al., "Glucuronidation of 6α-Hydroxy Bile Acids by Human Liver Microsomes," J. Clin. Invest., Jul. 1987, pp. 234-241, vol. 80.

Rettie, A. et al., "Hydroxylation of Warfarin by Human cDNA-Expressed Cytochrome P-450: A role for P-4502C9 in the Etiology of (S)-Warfarin-Drug Interactions," Chem. Res. Toxicol., 1992, pp. 54-59, vol. 5.

Ritter, J., "Roles of glucuronidation and UDP-glucuronosyltransferases in xenobiotic bioactivation reactions," Chem.-Biol. Interact., 2000, pp. 171-193, vol. 129.

Ravinet Trillou, C. et al., "Anti-obesity effect of SR 141716, a CB1 receptor antagonist; in diet induced obese mice," Am. J. Physiol. Regul. Integr. Comp. Physiol., Oct. 24, 2002, pp. R345-R353, vol. 284.

Wadelius, M. et al., "Association of warfarin dose with genes involved in its action or metabolism," Hum. Genet, 2007, pp. 23-34, vol. 121.

Wang, L. et al., "Identification of the Human Enzymes Involved in the Oxidative Metabolism of Dasatinib: An Effective Approach for Determining Metabolite Formation in Kinetics," Drug Metabolism and Disposition, 2008, pp. 1828-1839, vol. 36, No. 9.

Wienkers, L. et al., "Formation of R-(8)-hydroxywarfarin in human liver microsomes: A New Metabolic Marker for the (S)-mephenytoin hydroxylase, P4502C19," Drug Metab. Dispos., 1996, pp. 610-614 , vol. 24, No. 5.

Wen, Z.,et al., "UDPglucuronosyltransferase 1A1 is the principal enzyme responsible for etoposide glucuronidation in human liver and intestinal microsomes: structural characterization of phenolic and alcoholic Oucuronides of etoposide and estimation of enzyme kinetics," Drug Metab. Dispos., 2007, pp. 371-380, Vo. 35, No. 3.

Wittwer, E. et al., "Role of morphine's metabolites in analgesia: concepts and controversies," AAPS J., 2006, pp. E348-E352, vol. 8, No. 2, Article 39.

Xiong, Y. et al., "Phenylalanine 90 and 93 are localized within the phenol binding site of human UDPglucuronosyltransferase 1A10 as determined by photoaffinity labeling, mass spectrometry, and site-directed mutagenesis," Biochemistry, 2006, pp. 2322-2332, vol. 45.

Yamamoto, I. et al., "The pharmacological activity of cannabinol and its major metabolite, 11-hydroxycannabinol," Chem. Pharm. Bull., 1987, pp. 2144-2147, vol. 35, No. 5.

Zielinska, A. et al., "Glucuronidation of Monohydroxylated Warfarin Metabolites by Human Liver Microsomes and Human Recombinant UDP-Glucuronosyltransferases," J. Pharmacol. Exp. Therap., 2008, pp. 139-148, vol. 324, No. 1.

Zhang, Z. et al., "Human Cytochromes P4501A1 and P4501A2: R-warfarin Metabolism as a probe," Drug Metab. Dispos., 1995, pp. 1339-1345, vol. 23, No. 12.

Wu, L. et al., "Evidence for the Role of Reactive Nitrogen Species in Polymicrobial Sepsis-Induced Renal Peritubular Capillary Dysfunction and Tubular Injury," J. Am. Soc. Nephrol., 2007, pp. 1807-1815, vol. 18.

Battaglia, E. et al., "Characterization of a new class of inhibitors of the recombinant human liver UDP-glucuronosyltransferase, UGT1*6," Biochim. Biophys.Acta., Jan. 18, 1995, pp. 9-14, vol. 1243, No. 1.

Gall, W., et al., "Differential glucuronidation of bile acids, androgens and estrogens by human UGT1A3 and 2B7," J. Steroid Biochem. and Mol. Biol., 1999, pp. 101-108, vol. 70.

Kuzmic, P., "Program DYNAFIT for the Analysis of Enzyme Kinetic Data: Application to HIV Protease," Analytical Biochem., 1996, pp. 260-273, vol. 237, Article No. 0238.

Larkin, M. et al., "Clustal W and Clustal X version 2.0," Bioinformatics, 2007, pp. 2947-2948, vol. 23, No. 21.

Little, J. et al., "Characterization of Human Liver Microsomal UDP-Glycosyltransferases using Photoaffinity Analogs," J. Pharmacol. Exp. Ther., 1995, pp. 1551-1559, vol. 273, No. 3.

Miley, M., et al., "Crystal Structure of the Cofactor-Binding Domain of the Human Phase II Drug-Metabolism Enzyme UDP-Glucuronosyltransferase 2B7," J. Mol. Biol., Jun. 1, 2007, pp. 498-511, vol. 369, No. 2.

Offen, W. et al., "Structure of a flavonoid glucosyltransferase reveals the basis for plant natural product modification," Embo. J., 2006, pp. 1396-1405, vol. 25, vol. 6.

Paul, P. et al., "Synthesis and Characterization of a New Class of Inhibitors of Membrane-associated UDP-Glycosyltransferases," J. Biol. Chem., Jun. 15, 1993, pp. 12933-12938, vol. 268, No. 17.

Radominska, A. et al., "Characterization of UDP-glucuronic acid transport in rat liver microsomal vesicles with photoaffinity analogs," Biochim. Biophys. Acta, Oct. 12, 1994, pp. 63-70, vol. 1195, No. 1.

Radominska-Pandya, A. et al., "Structural and Functional Studies of UDP-Glucuronosyl Transferases," Drug Metab. Rev., 1999, pp. 817-899, vol. 31, No. 4.

Reynolds, K. et al., "Individualizing warfarin therapy," Personalized Medicine, 2007, pp. 11-31, vol. 4, No. 1.

Šali, A. et al., "Comparative Protein Modelling by Satisfaction of Spatial Restraints," J. Mol. Biol., Dec. 5, 1993, pp. 779-815, vol. 234, No. 3.

Moran, J. et al., "LC-Ms/ms Characterization of Warfarin Metabolites Excreted in Human Urine," Oct. 3, 2008, Abstracts, 64th Southwest Regional Meeting of the ACS, 1 page.

NYU Medical Center, Patient & Family Education, "Managing Your Warfarin (Coumadin®) Therapy A Patient's Guide," Mar. 2002, 15 pages.

Office Action dated Aug. 1, 2012 for related U.S. Appl. No. 12/766,635; 12 pages.

Smith, S. et al., "Plasma pharmacokinetics of warfarin enantiomers in cats," J. Vet. Pharmacol. Ther., Dec. 2000, pp. 329-337, vol. 23, No. 6 (abstract only; 1 page).

International Search Report and Written Opinion mailed Jun. 6, 2012 for related International Patent Application No. PCT/US2012/026578; 10 pages.

Jones, D. et al., "Warfarin and UDP-glucuronosyltransferases: writing a new chapter of metabolism," Drug Metabolism Reviews, 2010, pp. 55-61, vol. 42, No. 1.

Locatelli, I. et al., "Determination of warfarin enantiomers and hydroxylated metabolites in human blood plasma by liquid chromatography with achiral and chiral separation," Journal of Chromatography B, 2005, pp. 191-198, vol. 818.

Newton, D. et al., "Evaluation of Specificities in the In Vitro Metabolism of Therapeutic Agents by Human Liver Microsomes," Drug Metabolism and Disposition, 1995, pp. 154-158, vol. 23, No. 1.

Panyam, J. et al., "Biodegradable nanaparticles for drug and gene delivery to cells and tissue," Advanced Drug Delivery Reviews, 2003, pp. 329-347, vol. 55.

Steward, D. et al., "Genetic association between sensitivity to warfarin and expression of CYP2C9*3," Pharmacogenetics, Oct. 1997, pp. 361-367, vol. 7, No. 5 (Abstract Only, 1 page).

Takahashi, H. et al., "Comparisons between in-vitro and in-vivo metabolism of (S)-warfarin: catalytic activities of cDNA-expressed CYP2C9, its Leu359 variant and their mixture versus unbound clearance in patients with the corresponding CYP2C9 genotypes," Pharmacogenetics, Oct. 1998, pp. 365-373, vol. 8, No. 5 (Abstract Only, 2 pages).

* cited by examiner

CLASSICAL CANNABINOID METABOLITES AND METHODS OF USE THEREOF

CROSS REFERENCE TO RELATED APPLICATIONS

This application claims the priority of U.S. Provisional Application Ser. No. 61/236,298, filed Aug. 24, 2009, which is hereby incorporated by reference in its entirety.

GOVERNMENTAL RIGHTS

This invention was made with government support under RO1 GM075893-05 awarded by the National Institutes of Health. The government has certain rights in the invention.

FIELD OF THE INVENTION

The present invention encompasses classical cannabinoid metabolites and uses thereof.

BACKGROUND OF THE INVENTION

The activity of pharmaceutical compounds is modulated, in part, by their metabolic inactivation and elimination. As a result, understanding the metabolic pathways associated with the inactivation and elimination of a compound provides valuable information about the pharmacokinetics of the compound. Generally speaking, metabolism of a compound comprises two phases. Phase I reactions usually precede Phase II, though not necessarily. During phase I reactions, polar bodies are either introduced or unmasked, which results in (more) polar metabolites of the original compound. During phase II reactions, a watersoluble moiety is conjugated to a polar body introduced or unmasked during phase I.

Phase II may involve UDP-glucuronosyltransferases (UGTs), which are extensively involved in the overall metabolism and disposition of endo- and xenobiotics. UGTs catalyze the transfer of the glucuronosyl group from uridine 5'-diphospho-glucuronic acid (UDP-glucuronic acid) to substrate molecules that contain oxygen, nitrogen, sulfur or carboxyl functional groups. Glucuronidation of a compound may modulate the bioavailability, activity, and clearance rate of a compound.

As a result, there is a need in the art to identify phase II metabolic compounds. Additionally, there is a need for methods of detecting, quantifying, and manipulating the production of these compounds.

SUMMARY OF THE INVENTION

One aspect of the present invention encompasses an isolated classical cannabinoid glucuronide.

Another aspect of the present invention encompasses a combination of a classical cannabinoid glucuronide and a compound selected from the group consisting of an analgesic, an anti-convulsant, an anti-inflammatory, an anti-anxiety compound, and an anti-emetic compound.

Yet another aspect of the present invention encompasses a method of detecting a classical cannabinoid glucuronide in a sample, the method comprising liquid chromatography followed by mass spectrometry, wherein the total chromatography run time is less than about eighteen minutes.

Still another method of the invention encompasses a classical cannabinoid metabolic profile of a subject. The profile typically comprises the identity and quantity of phase II classical cannabinoid metabolites in a sample from a subject.

Other aspects and iterations of the invention are described more thoroughly below.

DETAILED DESCRIPTION OF THE INVENTION

Figure 1:
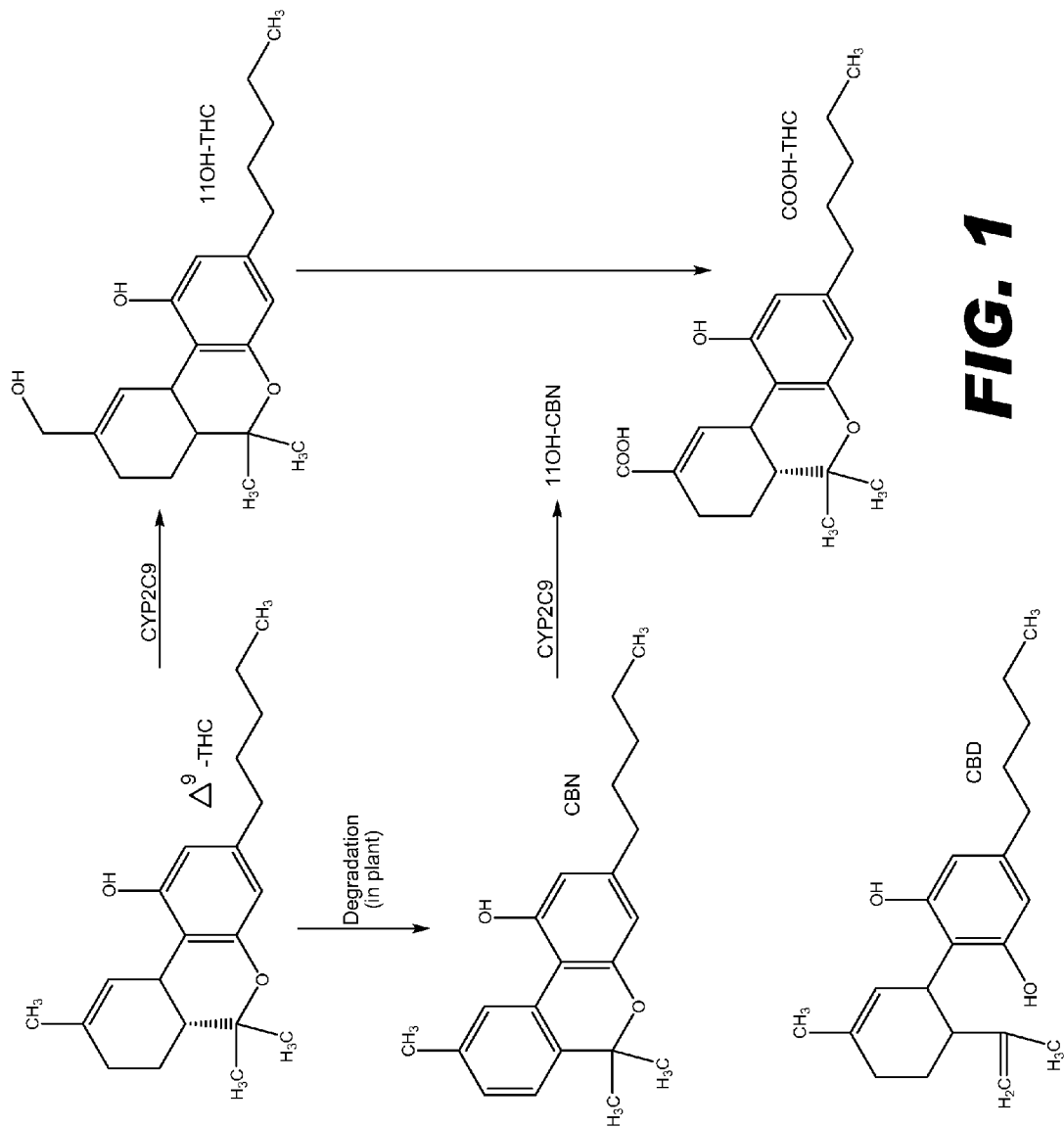
FIG. 1 depicts the structures of several cannabinoids.

The present invention encompasses classical cannabinoid metabolites, methods of making classical cannabinoid metabolites, methods of detecting classical cannabinoid metabolites, classical cannabinoid metabolic profiles, and methods of using such metabolites and profiles.

I. Classical Cannabinoid Metabolites

One aspect of the present invention encompasses an isolated classical cannabinoid metabolite. The metabolite may be a phase I or a phase II metabolite. In an exemplary embodiment, the metabolite is a classical cannabinoid glucuronide. As used herein, a "classical cannabinoid" refers to a cannabinoid that is structurally similar to tetrahydrocannabinol (THC) and can bind to a cannabinoid receptor. Non-limiting examples may include cannabinol (CBN), cannabidiol (CBD), (−)-$\Delta^8$-THC, and (−)-$\Delta^9$-THC. Additional examples may also include CBG, CBC, CBL, and CBV. The term "classical cannabinoid" also encompasses metabolites of a classical cannabinoid, such as (±)-11-hydroxy-$\Delta^9$-THC (11-OH-THC) and (−)-11-nor-9-carboxy-$\Delta^9$-THC(COOH-THC). In still another embodiment, the term classical cannabinoid metabolite may encompass a product of a reaction of THC with CYP2C9 or CYP3A4. Hence, the invention encompasses an isolated glucuronide derivative of any of the above compounds.

In one embodiment, the invention encompasses $\Delta^9$-THC glucuronidated at the C1 position. In another embodiment, the invention encompasses CBN glucuronidated at the C1 position. In yet another embodiment, the invention encompasses CBD glucuronidated at the C1 or C5 positions. In still another embodiment, the invention encompasses THC-OH glucuronidated on the allylic side chain or the phenolic group, or a combination thereof. In some embodiments, the invention encompasses THC-COOH glucuronidated on the carboxyl terminus or the phenolic group, or a combination thereof.

In additional embodiments of the invention, classical cannabinoid metabolites of the invention may be labeled. Suitable labels are known in the art, and may include labels for mass spectrometry or other detection means. In other embodiments, classical cannabinoid metabolites, such as glucuronides, may be used as standards. In one embodiment, a labeled classical cannabinoid metabolite may be used as a standard. In an exemplary embodiment, a labeled classical cannabinoid glucuronide may be used as a standard.

(a) Methods of Synthesis

The invention also encompasses methods of synthesizing a classical cannabinoid glucuronide. Generally speaking, the method comprises exposing a classical cannabinoid or a classical cannabinoid metabolite to a UDP-glucuronosyltransferase (UGT). Non-limiting examples of UGTs may include UGT1A1, UGT1A3, UGT1A4, UGT1A6, UGT1A7, UGT1A8, UGT1A9, UGT1A10, UGT2B4, UGT2B7, UGT2B15, and UGT2B17. The UGT may be a recombinant UGT. Methods of making recombinant UGTs are known in the art.

In one embodiment, a glucuronide of COOH-THC may be synthesized by exposing COOH-THC to UGT1A1 or UGT1A3. In another embodiment, a glucuronide of 11-OH-THC may be synthesized by exposing 11-OH-THC to UGT1A9 or UGT1A10. In yet another embodiment, a glucuronide of CBN may be synthesized by exposing CBN to UGT1A10, UGT1A7, UGT1A9, or UGT2B7. In still another embodiment, a glucuronide of CBD may be synthesized by exposing CBD to UGT1A9, UGT2B7, or UGT2B17. For more details, see the Examples.

(b) Pharmaceutical Compositions

Another aspect of the present invention encompasses a pharmaceutical composition comprising a classical cannabinoid metabolite. In one embodiment, the pharmaceutical composition comprises a classical cannabinoid glucuronide and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the classical cannabinoid glucuronide.

The pharmaceutical compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application.

Pharmaceutical compositions may be sterile and are typically stable under conditions of manufacture and storage. The composition may be formulated as a solution, microemulsion, dispersion, liposome, or other ordered structure suitable to high drug concentration. Sterile injectable solutions can be prepared by incorporating the active compound (i.e., classical cannabinoid glucuronide) in the required amount in an appropriate solvent with one or a combination of ingredients enumerated above, as required, followed by filtered sterilization. Generally, dispersions are prepared by incorporating the active compound into a sterile vehicle that contains a basic dispersion medium and one or more potential other ingredients from those detailed above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution may be maintained, for example, by the use of a coating such as lecithin, by the maintenance of the required particle size in the case of dispersion and by the use of surfactants. Prolonged absorption of injectable compositions may be achieved by including an agent that delays absorption, for example, monostearate salts and gelatin, in the composition.

A pharmaceutical composition comprising a classical cannabinoid glucuronide may be administered to a subject. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are generally known to those skilled in the art. See, e.g., Sustained and Controlled Release Drug Delivery Systems, J. R. Robinson, ed., Marcel Dekker, Inc., New York, 1978.

In certain embodiments, a compound of the invention may be orally administered, for example, with an inert diluent or an assimilable edible carrier. The composition (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

(c) Methods of Use

The present invention also encompasses methods of use for a classical cannabinoid glucuronide. In one embodiment, the invention provides a method of treating pain. In another embodiment, the invention provides a method of treating a malady from the group comprising convulsion, inflammation, anxiety, and nausea. Generally speaking, a method of the invention comprises administering a classical cannabinoid glucuronide to a subject in need thereof. Methods of administration may be found in section I (b) above.

(d) Combinations

The present invention further encompasses combinations of classical cannabinoid glucuronides with other analgesics, anti-convulsants, anti-inflammatories, anti-anxiety compounds, or anti-emetic compounds. For instance, a combination of the invention may comprise a classical cannabinoid glucuronide and an opiod agonist, such as alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. A combination may also comprise a classical cannabinoid glucuronide and a non-opiod analgesic, which may include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, pharmaceutically acceptable salts thereof, and mixtures thereof. Other suitable non-opioid analgesics may include the following, non-limiting, chemical classes of analgesic, antipyretic, nonsteroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, Analgesic-Antipyretic and Anti-inflammatory Agents and Drugs Employed in the Treatment of Gout, in Goodman & Gilman's The Pharmacological Basis of Therapeutics 617-57 (Perry B. Molinhoff and Raymond W. Ruddon eds., 9th ed 1996) and Glen R. Hanson, Analgesic, Antipyretic and Anti-Inflammatory Drugs in Remington: The Science and Practice of Pharmacy Vol II 1196-1221 (A. R. Gennaro ed. 19th ed. 1995) which are hereby incorporated by reference in their entireties. Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, rofecoxib and celecoxib. The amount of an analgesic agent included in a combination detailed above may be readily determined by one of skill in the art.

Suitable anticonvulsants may include aldehydes, aromatic allylic alcohols, barbiturates, benzodiazepines, bromides, carbamates, carboxamides, fatty acids, fructose derivatives, gaba analogs, hydantoins, oxazolidinediones, propionates, pyrimidinediones, pyrrolidines, succinimides, sulfonamides, triazines, ureas and valproylamides. The amount of an anticonvulsant agent included in a combination of the invention may be readily determined by one of skill in the art.

Suitable anti-anxiety compounds may include benzodiazepines, SSRIs, azapirones, barbiturates, hydroxyzine, and pregabalin. The amount of an anti-anxiety compound included in a combination of the invention may be readily determined by one of skill in the art.

Combinations of a classical cannabinoid metabolite and an anti-emetic may include 5-HT3 receptor antagonists such as dolasetron, granisetron, ondansetron, tropisetron, and palonosetron; dopamine antagonists, such as domperidone, droperidol, haloperidol, chlorpromazine, promethazine, prochlorperazine, metoclopramide, and alizapride; antihistamines (H1 histamine receptor antagonists) such as cyclizine, diphenhydramine, dimenhydrinate (Gravol), meclizine, promethazine (pentazine, phenergan, promacot), and hydroxyzine; benzodiazepines, such as midazolam and lorazepam; anticholinergics such as hyoscine (also known as scopolamine); steroids such as dexamethasone; trimethobenzamide; ginger; emetrol; propofol given intravenously; peppermint; or other suitable anti-nasea or anti-vomiting agents. The amount of an anti-emetic agent included in a combination of the invention may be readily determined by one of skill in the art.

In some embodiments, a combination of the invention may be administered as described in section I(b) above. In one embodiment, a combination may be administered such that both compounds are administered simultaneously. Alternatively, a combination may be administered such that both compounds are administered sequentially. During sequential administration, the time between the first compound is administered and the second compound is administered may be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 min. In another embodiment, the time between the first compound is administered and the second compound is administered may be about 1, 2, 3, 4, 5, 6, 7, 8, 9, 10, 11, 12, 13, 14, 15, 16, 17, 18, 19, 20, 21, 22, 23, or 24 hrs. In still another embodiment, the time between the first compound is administered and the second compound is administered may be about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, days. In yet another embodiment, the time between the first compound is administered and the second compound is administered may be about 1, 2, 3, or more than 3 months. A classical cannabinoid glucuronide may be the first compound or the second compound administered in a combination administered sequentially.

A combination of the invention may be a pharmaceutical composition as detailed in section 1(b).

II. Metabolic Profile

Another aspect of the present invention encompasses a metabolic profile of a classical cannabinoid in a sample from a subject. As used herein, a "metabolic profile" refers to the identity and quantity of at least one metabolite of a classical cannabinoid in a sample from a subject. In an exemplary embodiment, the metabolic profile is stored on a computer-readable medium. A metabolic profile may comprise phase I metabolites and/or phase II metabolites. Phase I metabolites are the products of phase I metabolic reactions. Phase I metabolic reactions generally introduce or unmask polar groups, which results in (more) polar metabolites of the original compound. Phase II reactions, also known as conjugation reactions (e.g., with glucuronic acid, sulfonates, glutathione or amino acids) generally involve interactions with the polar functional groups of phase I metabolites.

In one embodiment, the invention provides a metabolic profile of THC in a subject. A metabolic profile of THC may comprise products of phase I and/or phase II THC metabolism. Similarly, the invention encompasses a metabolic profile of CBD, CBN, and/or other classical cannabinoids. A method for determining the identity and quantity of classical cannabinoid metabolites is detailed in section II(b) below, and in the Examples.

Suitable samples for determining a metabolic profile may include tissue samples and fluid samples. For instance, non-limiting examples of fluid samples may include urine samples, plasma samples, whole-blood samples, and serum samples. Non-limiting examples of tissue samples may include biopsy samples, fresh frozen samples, or other tissue samples from a subject. In certain embodiments, the tissue samples are liver samples or intestinal samples. In an exemplary embodiment, the sample is a urine or plasma sample.

(a) Database

The invention also encompasses a database. Generally speaking, a database of the invention comprises at least one metabolic profile of a subject, and is typically stored on a computer-readable medium. A database may comprise more than one metabolic profile for a given subject over time (a "subject" database). Alternatively, a database may comprise a metabolic profile of a classical cannabinoid in a subject correlated to an effective dose range for the compound in the subject (a "dose" database). For instance, the database may comprise at least one classical cannabinoid metabolic profile of a subject, wherein the profile is correlated to one or more effective classical cannabinoid doses for the subject. Each of these databases is discussed in more detail below.

A database of the invention may also comprise background data on a subject. Non-limiting examples of background data may include age, weight, gender, race, ethnicity, diet, socio-economic status, current and/or past medications the subject has been exposed to, and the health status of the subject, including diseases or disorders that the subject may have.

i. Subject Database

A subject database may comprise at least one metabolic profile of one or more classical cannabinoids in a subject over time. For example, a subject database may comprise a metabolic profile from 2, 3, 4, 5, 6, 7, 8, 9, 10, 11, 12, 13, 14, 15, 16, 17, 18, 19, 20, or more than 20 time points for each classical cannabinoid. In one embodiment, the invention encompasses a subject database that comprises a classical cannabinoid metabolic profile for the subject from at least two different time points. In another embodiment, the invention encompasses a subject database that comprises a classical cannabinoid metabolic profile for the subject from at least 3, 4, 5, 6, 7, 8, 9, 10, 11, 12, 13, 14, 15, 16, 17, 18, 19, 20, or more than 20 time points. The time points may be minutes apart, hours apart, days apart, months apart, or years apart.

In a further embodiment, a database of the invention may comprise multiple subject databases.

ii. Dose Database

As stated above, a dose database may comprise a metabolic profile of a classical cannabinoid in a subject correlated to an effective dose range for the compound in the subject. Such a database may be used for determining the effective dose of a classical cannabinoid as detailed in section II(c) below. A dose database may comprise a metabolic profile of a classical cannabinoid correlated to an effective dose range for the compound for at least 1, 2, 3, 4, 5, 6, 7, 8, 9, 10, or more than 10 subjects. In certain embodiments, a database may comprise at least 20, 30, 40, 50, 60, 70, 80, 90, 100, or more than 100 subjects. In other embodiments, a database may comprise at least 100, 200, 300, 400, 500, 600, 700, 800, 900, 1000, or more than 1000 subjects.

In one embodiment, a classical cannabinoid dose database is comprised of phase I classical cannabinoid metabolic profiles. In yet another embodiment, a classical cannabinoid dose database is comprised of phase II classical cannabinoid metabolic profiles. In still another embodiment, a classical cannabinoid dose database is comprised of phase I and phase II classical cannabinoid metabolic profiles.

(b) Methods of Determining a Metabolic Profile

Another aspect of the present invention encompasses a method for determining a metabolic profile of a subject. The method comprises determining the identity and quantity of at least one metabolite of a classical cannabinoid in a sample from a subject. For instance, in some embodiments, the method may be used to determine the identity and quantity of at least one phase I metabolite of a classical cannabinoid. In other embodiments, the method may be used to determine the identity and quantity of at least one phase II metabolite of a classical cannabinoid. In another embodiment, the method may be used to determine the identity and quantity of at least one phase I and at least one phase II metabolite of a classical cannabinoid.

Generally speaking, the identity and quantity of a metabolite may be determined utilizing liquid chromatography followed by mass spectrometry. In some embodiments, the liquid chromatography is high performance liquid chromatography (HPLC). Non-limiting examples of HPLC may include partition chromatography, normal phase chromatography, displacement chromatography, reverse phase chromatography, size exclusion chromatography, ion exchange chromatography, bioaffinity chromatography, or aqueous normal phase chromatography. The mobile phase used in the HPLC may be a gradient.

In certain embodiments, the mass spectrometry may be tandem mass spectrometry. In some embodiments, the mass spectrometry may be quadrupole mass spectrometry. In alternative embodiments, other detection means may be employed, such as fluorescence, UV-Vis, or a chiral detector. In an exemplary embodiment, the method comprises HPLC followed by tandem mass spectrometry. In a further exemplary embodiment, the method may comprise HPLC followed by quadrupole tandem mass spectrometry. In each of the above embodiments, the liquid chromatography followed by mass spectrometry may also be used to determine the quantity of an identified metabolite in a metabolic profile.

Suitable samples for the method may include tissue samples and fluid samples from a subject. For instance, non-limiting examples of fluid samples may include urine samples, plasma samples, whole-blood samples, and serum samples. Non-limiting examples of tissue samples may include biopsy samples, fresh frozen samples, or other tissue samples from a subject. For instance, liver and/or intestinal samples may be suitable. In an exemplary embodiment, the sample is a urine or plasma sample. Generally speaking, the classical cannabinoid should be administered to the subject before the sample is collected. In some embodiments, the compound should be administered to the subject minutes, hours, days, weeks, and/or months before a sample is collected.

In particular embodiments, a method of the invention may be used to determine a classical cannabinoid metabolic profile in a sample from a subject. In one embodiment, the method comprises determining the identity and quantity of one or more phase I metabolites of a classical cannabinoid in a sample from a subject. In another embodiment, the method comprises determining the identity and quantity of one or more phase II metabolites of a classical cannabinoid, such as glucuronides. In yet another embodiment, the method comprises determining the identity and quantity of a classical cannabinoid, one or more phase I metabolites, and one or more phase II metabolites of a classical cannabinoid.

As described above, liquid chromatography followed by mass spectrometry may be used to determine the identity and quantity of a classical cannabinoid metabolite. Typically, the liquid chromatography comprises HPLC. The mobile phase for the HPLC is generally a gradient comprised of two different solutions: A and B. In one embodiment, A is comprised of water. In another embodiment, A is comprised of 5 mM ammonium acetate in water. In yet another embodiment, B may be an organic solvent miscible in water. Examples of such solvents may include acetonitrile, methanol, THF, or isopropanol. In certain embodiments, B may be acetonitrile.

The gradient of the mobile phase generally varies from about 50% B to about 100% B. In some embodiments, the gradient sequentially comprises (a) about 50% A and about 50% B, (b) a gradient from about 50% to about 60% B, (c) a gradient from about 60% to about 90% B, (d) a gradient from about 90% to about 100% B, (e) about 100% B, (f) a gradient from about 100% to about 50% B, and (g) about 50% B. Generally speaking, the flow time for step (a) above is about 0 to about 5 seconds, the flow time for step (b) is about 0 seconds to about 4 min, the flow time for step (c) is about 1 min to about 4 minutes, the flow time for step (d) is about two minutes to about five minutes, the flow time for step (e) is about 3 min to about nine minutes, the flow time for step (f) is about seven min to about eight minutes thirty seconds, and the flow time for step (g) is about seven min to about nine minutes or more.

In certain embodiments, the gradient comprises about 50% A and about 50% B for about the first 0 s, a linear gradient from about 50% to about 60% B (for about 0 to about 2 min), a linear gradient from about 60% to about 90% B (for about 2 to about 3 min), a linear gradient from about 90% B to about 100% B (for about 3 to about 4.1 min), about 100% B maintained for between about 4.1 min to about 7.9 min), a linear gradient from about 100% to about 50% B (for about 7.9 to about 8.0 min), and about 50% B for about 8.0 min or longer.

Usually, the flow time is less than 20 min. In some embodiments, the flow time is about 20, 19, 18, 17, 16, 15, 14, 13, 12, 11, 10, or less than 10 minutes. In some embodiments, the flow rate may be between about 0.1 ml/min and about 0.5 ml/min. In other embodiments, the flow rate may be about 0.25 mL/min.

The temperature may typically be between about 25° C. and 50° C. In one embodiment, the temperature may be about 35, 36, 37, 38, 39, 40, 41, 42, 43, 44, or 45° C. In another embodiment, the temperature may be about 40° C.

The mass spectrometry settings are detailed in the Examples.

(c) Uses for a Metabolic Profile

Still another aspect of the invention encompasses uses for a metabolic profile. Non-limiting examples of uses for a metabolic profile are detailed below.

i. Determining an Effective Dose Range of a Classical Cannabinoid

In one embodiment, the invention provides a method for determining an effective dose range of a classical cannabinoid. The method comprises, in part, determining the metabolic profile of a subject for a classical cannabinoid. Then the profile may be compared to a dose database for the particular classical cannabinoid. Stated another way, the profile may be compared to a database comprising at least one metabolic profile for the classical cannabinoid correlated to a known effective dose of the compound. A database profile similar to the subject's profile may then be selected, wherein the effective dose range correlated to the database profile is the effective dose range for the subject.

ii. Screening for Compounds that Modulate the Metabolism of a Classical Cannabinoid Another embodiment of the invention comprises a method of screening for compounds that modulate the metabolism of a classical cannabinoid. The method typically comprises determining the metabolic profile of a first classical cannabinoid in a subject, administering a second compound to the subject, and detecting a change in the metabolic profile of the first classical cannabinoid. A change in the profile indicates that the second compound modulates the metabolism of the first compound. In certain embodiments, the second compound may be another classical cannabinoid, a food ingredient, an environmental compound, or a metabolite of the first compound. The change in the profile may be a change in the presence and/or absence of a metabolite, or may be a change in the quantity and/or ratio among the metabolites.

iii. Detecting Changes in a Classical Cannabinoid's Metabolism

Yet another embodiment of the invention encompasses a method for determining changes in the metabolism of a classical cannabinoid in a subject over time. The method generally comprises determining a metabolic profile for the compound in a subject at a first time point and at least one other time point. The profiles from the two time points may be compared, such that a change in the profile may indicate a change in the metabolism of the classical cannabinoid. In some embodiments, the method may comprise comparing profiles from 2, 3, 4, 5, 6, 7, 8, 9, 10, or more time points. The time points may be days apart, weeks apart, months apart, or years apart.

The profiles from the first and any subsequent time points may be stored in a subject database, as described above.

Definitions

As used herein, "computer-readable medium" refers to a medium that participates in providing instructions to a processor for execution. Such a medium may take many forms, including but not limited to non-volatile media, volatile media, and transmission media. Non-volatile media may include, for example, optical or magnetic disks. Volatile media may include dynamic memory. Transmission media may include coaxial cables, copper wire and fiber optics. Transmission media may also take the form of acoustic, optical, or electromagnetic waves, such as those generated during radio frequency (RF) and infrared (IR) data communications. Common forms of computer-readable media include, for example, a floppy disk, a flexible disk, hard disk, magnetic tape, or other magnetic medium, a CD-ROM, CDRW, DVD, or other optical medium, punch cards, paper tape, optical mark sheets, or other physical medium with patterns of holes or other optically recognizable indicia, a RAM, a PROM, and EPROM, a FLASH-EPROM, or other memory chip or cartridge, a carrier wave, or other medium from which a computer can read.

As used herein, "effective dose" refers to the dose range of a classical cannabinoid that results in a desired pharmaceutical effect, without causing undue harm to the subject. Methods of determining an effective dose of a compound are known in the art.

As used herein, "metabolite" refers to a product of the metabolism of the compound. In certain embodiments where the parent compound may be found in a sample with metabolic products of the compound, the parent compound may also be referred to as a metabolite.

As used herein, "subject" refers to a mammal. In some embodiments, a suitable subject may include a laboratory animal, a companion animal, a livestock animal, a non-human primate, or a human. In an exemplary embodiment, a subject is a mammal that metabolizes a classical cannabinoid of interest. For example, to determine a classical cannabinoid metabolic profile in a subject, the subject typically should metabolize classical cannabinoid. The subject may be an infant, an adolescent, or an adult.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that may changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Introduction

*Cannabis sativa* has been used both therapeutically and recreationally for centuries, $\Delta^9$-Tetrahydrocannabinol ($\Delta^9$-THC) is the main psychoactive ingredient in marijuana and mediates its effects primarily through activation of two G-protein coupled receptors, $CB_1$ and $CB_2$ (Howlett, 1995). Identified in 1990 (Matsuda et al., 1990), the human $CB_1$ receptor was found to be primarily localized in central and peripheral nervous tissue (Herkenharn et al., 1990: Ishac et al., 1996). The $CB_1$ receptor has been identified as a therapeutic target in a variety of disease states, including obesity (Ravinet et al., 2002), alcohol dependence (Racz et al., 2003), pain (Iversen and Chapman. 2002) and Parkinson's disease (Brotchie, 2003), The second cannabinoid receptor, $CB_2$, cloned in 1993 (Munro et al, 1993) is found in immune tissues, most abundantly in the spleen and leukocytes (Galiegue et al., 1995). Selective $CB_2$ receptor ligands have potential therapeutic use as immune modulators for tumor suppression (Klein et al, 2003) and inflammation (Conti et al., 2002).

Cannabinoids typically encompass compounds that are either structurally similar to THC or ligands that bind to cannabinoid receptors. While THC-related compounds are referred to as classical cannabinoids (FIG. 1), ligands structurally distinct to THC also bind to $CB_1$ and/or $CB_2$ receptors and are classified as nonclassical cannabinoids, aminoalkylindoles and eicosanoids. The metabolism of the classical cannabinoids (the subject of this study) is very complex. For example, approximately 100 metabolites have thus far been identified for THC. The high lipid solubility of classical cannabinoids makes them good substrates for the cytochrome P450 mixed-function oxidases. Metabolism by CYP2C9 and CYP3A4 appears to account for most of the primary THC metabolites (Watanabe et al, 2007), For example, THC is hydroxylated at C11, at C8, and at all positions of the alkyl side-chain. C11 is the preferred hydroxylation site in man. In humans, CYP2C9 has been shown to catalyze the formation of the psychoactive 11-hydroxy metabolite of $\Delta^9$-THC (Bornheim et al., 1992; Watanabe et al., 1995), and CYP3A4 is responsible for hydroxylation at the 8β-position (Bornheim et al., 1992). Following the initial hydroxylation, many of the hydroxyl groups undergo further oxidation to primarily produce carboxylic groups at C11 and C5 (alkyl side chain). In contrast to phase 1 metabolism, very little is known about the phase II metabolism of classical cannabinoids. Phase II metabolites appear to be mainly conjugates of the phase I metabolites with glucuronic acid, catalyzed by the activity of UDP-glucuronosyltransferases (UGTs). For example, oxidation of the active metabolite $\Delta^9$-THC-OH leads to the inactive metabolite 11-nor-9-carboxy-$\Delta^9$-THC(COOH-THC), This modification of the cannabinoid also favors conjugation at the carboxyl position to form an O-esterglucuronide, which is the main metabolite found in urine (Yamamoto et al., 1987). Although phase II metabolism is generally thought of as a pathway to inactivate drugs, it is well known that this pathway may also result in metabolic activation.

To better understand this metabolic pathway, identification of the human UGTs involved in metabolism of classical cannabinoids and product characterizations are required. Therefore, the purpose of the present study was to characterize potential glucuronidated products produced by human liver microsomes and 12 human recombinant UGTs in the presence of THC derivatives, cannabinol (CBN), cannabidiol (CBD), (−)-$\Delta^8$-THC, (−)-$\Delta^9$-THC, (±)-11-hydroxy-$\Delta^9$-THC (11-OH-THC), and (−)-11-nor-9-carboxy-$\Delta^9$-THC(COOH-THC). Data show that both hepatic and extrahepatic UGTs selectively recognize certain cannabinoids for conjugation.

Materials and Methods

Materials

All chemicals used for this study were of at least reagent grade. Cannabinol (CBN), Cannabidiol (CBD), (−)-$\Delta^9$-THC, (±)-11-hydroxy-$\Delta^9$-THC, and (−)-11-nor-9-carboxy-$\Delta^9$-THC were purchased from Cerilliant (Round Rock, Tex.). [$^{14}$C]UDP-GlcUA (325 mCiimmol) was purchased from PerkinElmer Life Sciences (Boston, Mass.). Ethyl alcohol (95%) was purchased from AAPER (Shelbyville, Ky.). Unless otherwise specified, all other chemicals and reagents were of reagent gade and purchased from Sigma-Aldrich (St. Louis, Mo.).

Membrane fractions from baculovirus-infected insect cells expressing individual recombinant human UGTs were prepared as previously described (Kurkela et al., 2003; Kuuranne et al., 2003). Each enzyme tested in this study is known to be active toward substrates specific for that isoform. The expression level of individual recombinant UGTs was estimated by Western blot analyses using monoclonal antibodies (Tetra-His antibodies; Qiagen, Germany) against the His-tag that all of them carry (Kurkela et al., 2003). For activity comparison between individual UGTs, the enzyme level was normalized as previously described (Kuuranne et al., 2003).

Recombinant UGT Isoform Incubations

UGT activity was determined using [$^{14}$C]-UDP-GlcUA as the sugar donor for TLC analysis (Little et al., 2004) and unlabeled UDP-GlcUA for LC-MS/MS analysis. Briefly, UGT recombinant membrane protein (5 μg) was incubated in 100 μM Tris-HCl (pH 7.4)/5 mM $MgCl_2$/5 mM saccharolactone with 100 μM-2000 μM substrate, in a total volume of 30 μl, Substrates were added in DMSO with a final concentration of 2%, and controls omitting substrates were run with each assay. Reactions were started by the addition of the appropriate UDP-GlcUA co-substrate (4 mM) and incubated at 37° C. for 90 min (screening) and 30 min (kinetics). Reactions were stopped by addition of 40 µl of ethanol.

TLC Analysis

TLC analysis of glucuronidation products formed from [$^{14}$C]UDP-GlcUA were carried out as described previously (Radominska-Panyda et al., 1987), In brief, aliquots (60 µL) of each incubation were applied to the preabsorbent layer of channeled silica gel TLC plates (Baker 250Si-PA (19C); VWR Scientific, Sugarland, Tex.) and glucuronidated products and unreacted substrate were separated by development in chloroform-methanol-glacial acetic acid-water (65:25:2:4, v/v). Radioactive compounds were localized on TLC plates by autoradiography for 3-4 days at −80° C. Silica gel in areas corresponding to the glucuronide bands identified from autoradiograms and the corresponding areas from control lanes were scraped from the TLC plate into scintillation vials. and the radioactivity was measured by liquid scintillation counting (Packard TRI-GARB 2100TR, Perkin-Elmer). The results of these experiments were analyzed and apparent kinetic parameters were determined using Prism 4 software (GraphPad. San Diego, Calif.).

LC-MS/MS Analysis

Liquid chromatography-tandem mass spectrometry (LC-MS/MS) analyses for product confirmation were performed using an Agilent 1100 HPLC system (Santa Clara. Calif.) which was interfaced with an API 4000 triple quadrupole (MS/MS) mass spectrometer (Applied Biosystems. Foster City. Calif.). Instrument operation and data acquisition was controlled through the Analyst software package (Version 1.4.2, Applied Biosystems). The HPLC system consisted of an autosampler, a binary pump, and a column oven. Samples were loaded and resolved at a flow rate of 0.25 ml/min on a 4.0×50 mm phenyl column (YMC Phenyl 3 µm, Waters) maintained at 40° C. Mobile phases were 5 mM ammonium acetate (pH 6.5) in water (A) and acetonitrile (B). Compounds of interest were eluted using the following gradient: 50% B (0 min), linear gradient from 50% B to 60% B (0 to 2 min), linear gradient from 60% B to 90% B (2 to 3 min), linear gradient from 90% B to 100% B (3 to 4.1 min), 100% B (4.1 to 7.9 min), linear gradient from 100% B to 50% B (7.9 to 8 min), and 50% B (8.0 min. and after). Total run time, including a 2 min column pre-equilibration period, was 15 min. Injection volume was 5 µl. All MS/MS analyses were performed in negative ion mode by electrospray ionization (EI) using a Turbo IonSpray source. Curtain, nebulizer, turbo, and collisionally-activated dissociation gases were 40 psig, 50 psig, 65 psig, and 6 psig, respectively. Turbo heater temperature was 450° C., and ion spray voltage was −4500 V. Specific MS/MS experimental conditions are noted in Table 1.

TABLE 1

| | | | | | | | | |
|---|---|---|---|---|---|---|---|---|
| MS/MS Experimental Conditions for Product Ion, Multiple Reaction Monitoring (MRM), and Neutral Loss Studies | | | | | | | | |
| | | Analyte | Q1 (m/z) | Q3 (m/z) | CE$^a$ (V) | EP$^b$ (V) | DP$^c$ (V) | CXP$^d$ (V) |
| Production | 1 | CBN-Gloc | 485.1 | 50-525 | −20 to −35 | −10 | −50 to −70 | −9 to −15 (2 sec) |
| | 2 | THC-O-Glue | 505.3 | 50-510 | −30 to −40 | −10 | −50 to −70 | −9 |
| | 3 | THC-CO-O-Glue | 519.3 | 50-525 | −30 to −40 | −10 | −50 to −70 | −9 |
| MRM | 1 | CBN | 309.3 | 171.1 | −40 | −10 | −89 | −3 |
| | | | 309.3 | 279.2 | −42 | −10 | −91 | −7 |
| | 2 | .Δ9-THC | 313.3 | 191.2 | −38 | −10 | −87 | −3 |
| | | and CBD | 313.3 | 245.3 | −36 | −10 | −82 | −5 |
| | 3 | THC-OH | 329.3 | 268.3 | −38 | −10 | −69 | −6 |
| | | | 329.3 | 311.2 | −25 | −10 | −65 | −8 |
| | 4 | THC-COOH | 343.2 | 245.2 | −40 | −10 | −82 | −5 |
| | | | 343.2 | 299.3 | −29 | −10 | −75 | −7 |
| | 5 | CBN-Glucuronide | 485.1 | 113.2 | −29 | −10 | −61 | −8 |
| | | | 48.5.1 | 309.2 | −27 | −10 | −76 | −8 |
| | 6 | Δ9-THC-Gluc | 489.3 | 313.1 | −35 | −10 | −61 | −8 |
| | | and CBD-Gluc | 489.3 | 374.9 | −30 | −10 | −76 | −9 |
| | 7 | THC-OH Gluc | 503.3 | 311.2 | −44 | −10 | −56 | −8 |
| | | | 505.3 | 329.2 | −31 | −10 | −59 | −S |
| | 8 | THC-COO-Gluc | 519. | 193.2 | −25 | −10 | −47 | −8 |
| | | | 519.3 | 343.3 | −33 | −10 | −36 | −9 |
| Neutral Loss | 1 | Loss of glucuronio acid | Loss of 176 (400-800 amu) | | −20 to −35 | −10 | −50 to −80 | −9 to −15 (2 sec) |

$^a$Collision energy,
$^b$Entrance potential,
$^c$Declustering potential,
$^d$collision cell exit potential Example 1

Cannabinoid Glucuronidation by Human Hepatic Microsomes and Recombinant UGTs

Figure 2:
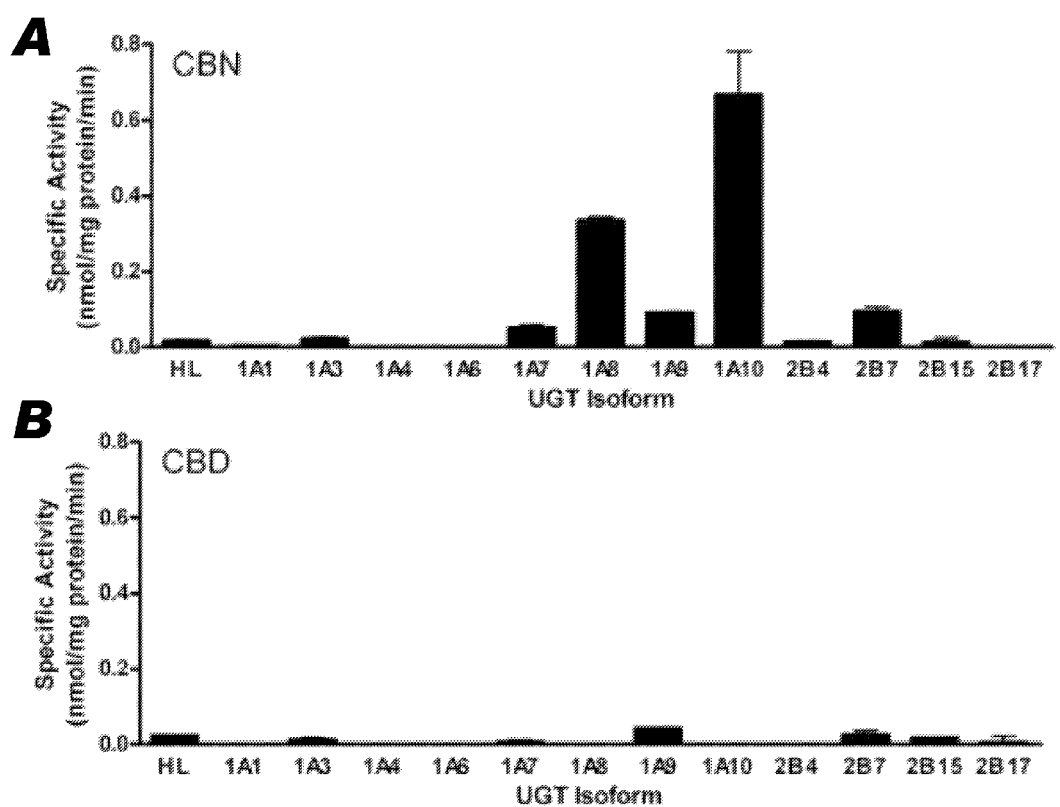
FIG. 2 depicts four graphs illustrating the glucuronidation activity screening. Selected recombinant UGT isoforms and human liver microsomes were screened for activity toward (A) CBN, (B) CBD, (C) COOH-THC, and (D) 11-OH-THC. Glucuronidation activities were measured by incubating microsomal protein (5 µg recombinant UGT: 50 µg HL) with substrate (500 µM) and UDP-GlcUA (4 mM). All reactions were normalized as described in the Examples.
Figure 2:
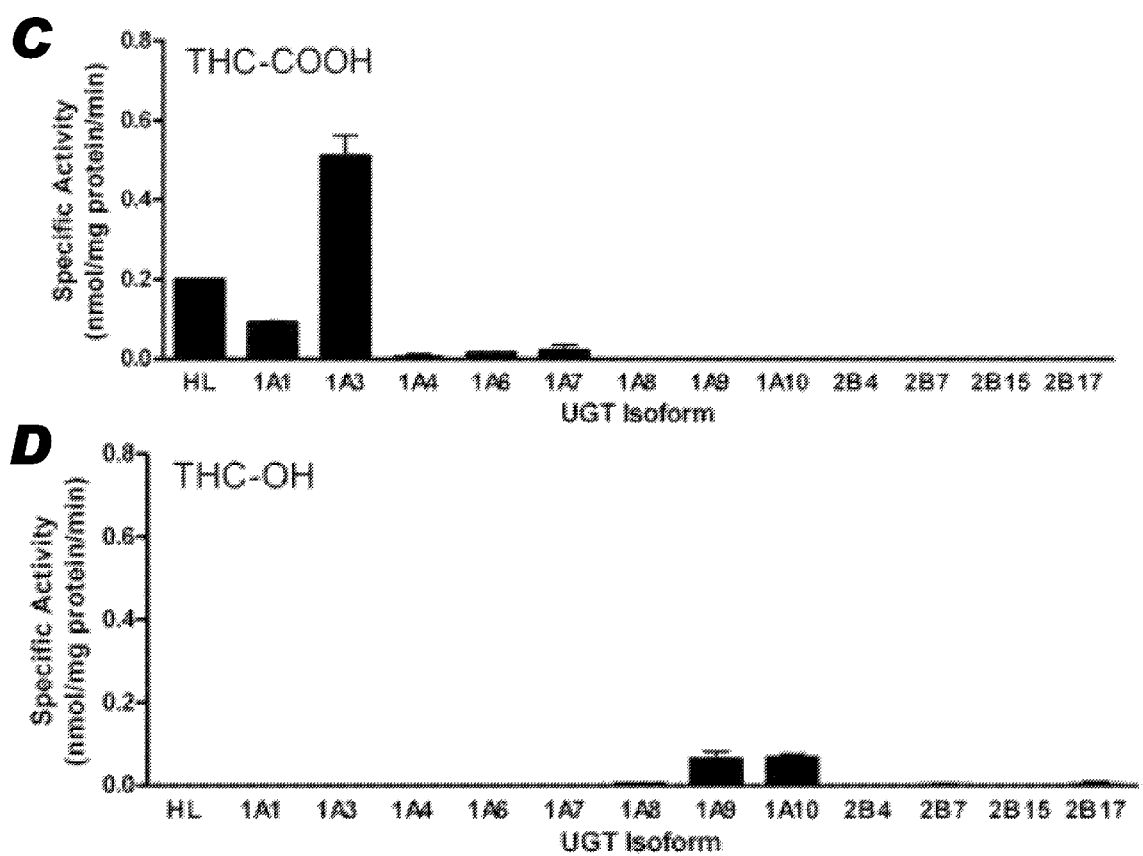

As an initial screen for glucuronidation activity toward cannabinoids, eight human recombinant UGT1A family UGTs expressed as His-tag proteins in baculovirus-infected Sf9 insect cells, four human recombinant UGT2B family over-expressed in HEK293 cells, and human liver microsomes were evaluated for their ability to glucuronidate 750 µM THC, CBN, CBD, (−)-Δ$^9$-THC, 11-OH-THC, or COOH-THC. (−)-Δ$^9$-THC did not appear to serve as a direct substrate for the tested human UGTs. This information indicates that native THC biotransformation is dependent on oxidations primarily catalyzed by CYP2C9 and CYP3A4 (Watanabe et al, 2007). UGT1A and 1B family isozymes showed variable responses in the presence of 11-OH-THC, COOH-THC, CBN, and CBD (FIG. 2). The major product of CYP2C9 metabolism, 11-OH-THC, was specifically glucuronidated via UGT1A9 and 1A10. The highest activity towards COOH-THC was observed with UGT1A3, but HLM and UGT1A1 also showed a significant amount of activity towards this substrate. CBN, the product of THC degradation, was glucuronidated at high levels by UGT1A10 and to a lesser extent by UGT1A7, 1A9, and 2B7. Activity toward CBD was limited. HLM and UGT1A9, 2B7, and 2B17 all formed a minimal amount of a glucuronidated CBD product.

Example 2

Product Confirmations/MS Spectral Interpretation

Figure 3:
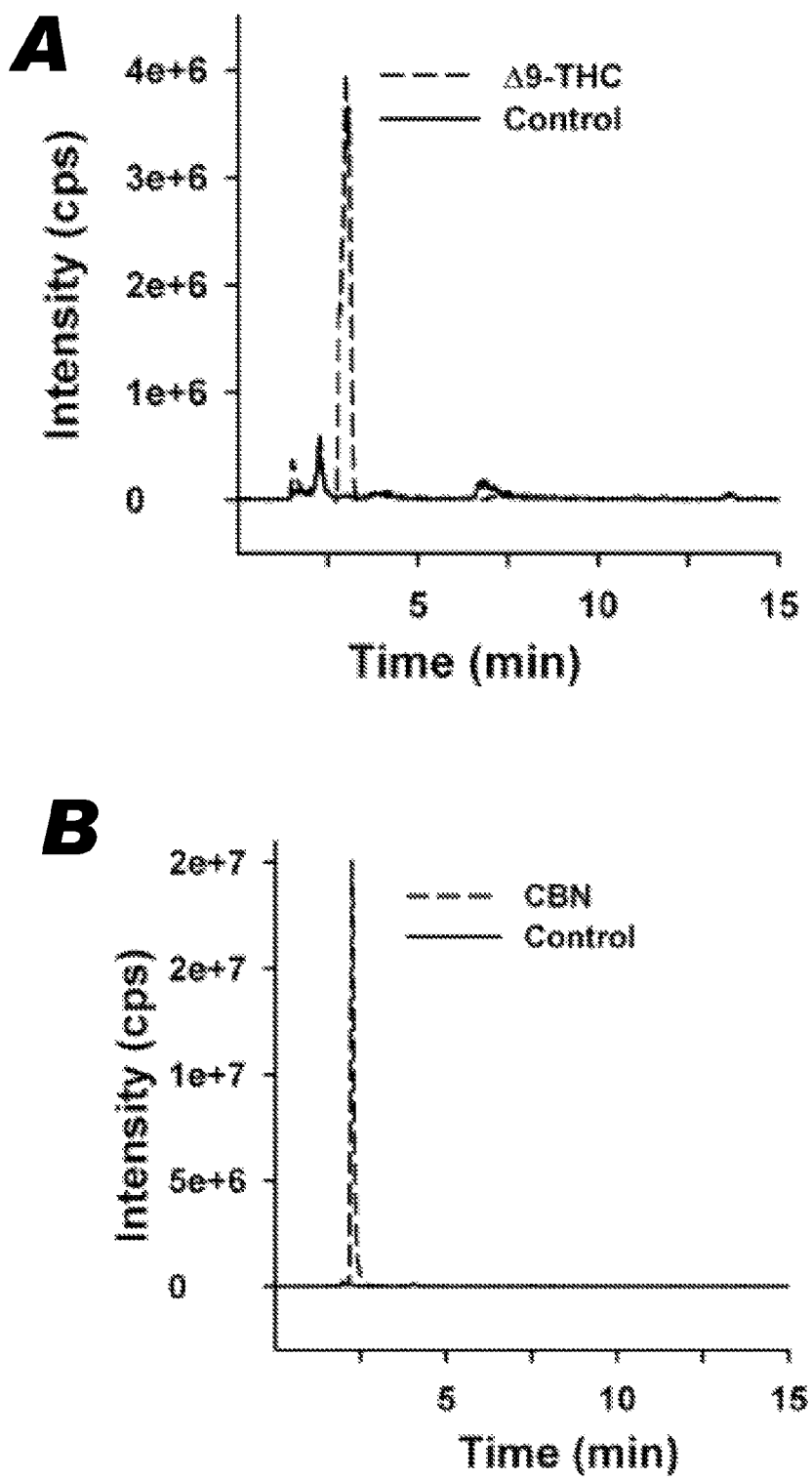
FIG. 3 depicts a series of graphs illustrating RP-HPLC chromatographs of glucuronidated-product ion experiments. Tracings represent organic-soluble metabolites generated during incubation of recombinant protein with UDP-glucuronic acid (4 mM) and 750 µM of each substrate (A) $\Delta^9$-THC, (B) CBN, (C) 11-OH-THC, (D) CBD, and (E) COOH-THC. Each substrate was incubated individually for 180 min. Control reactions omitted the respective substrate. MS/MS data were obtained in negative ion mode, as described in the Examples.
Figure 3:
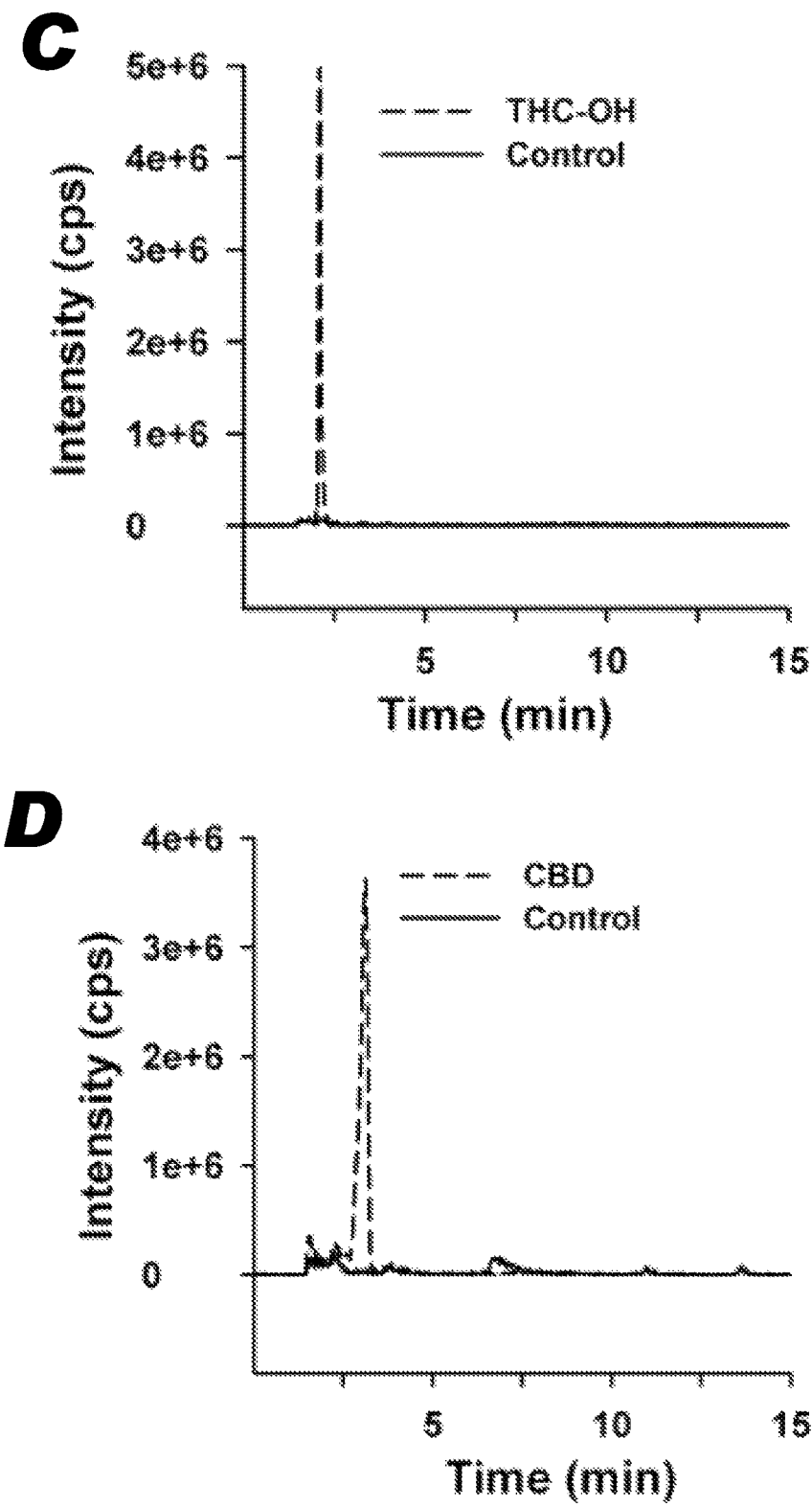
Figure 3E:
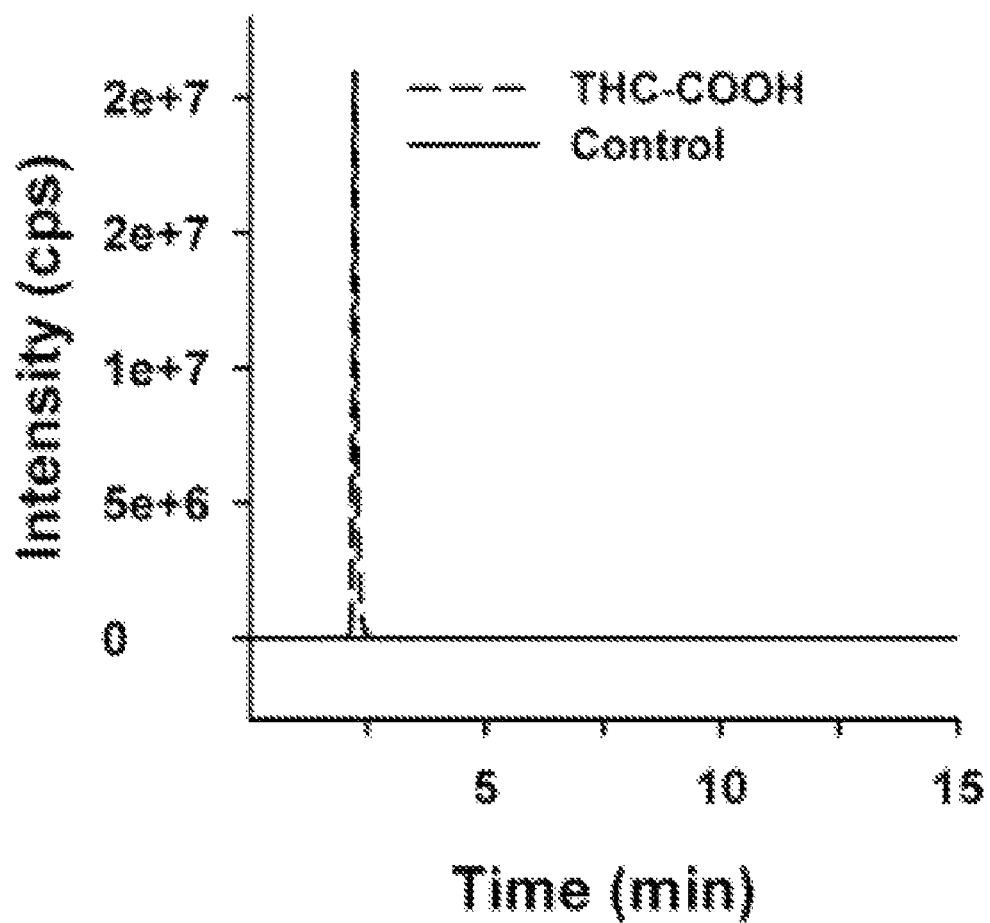
Figure 4:
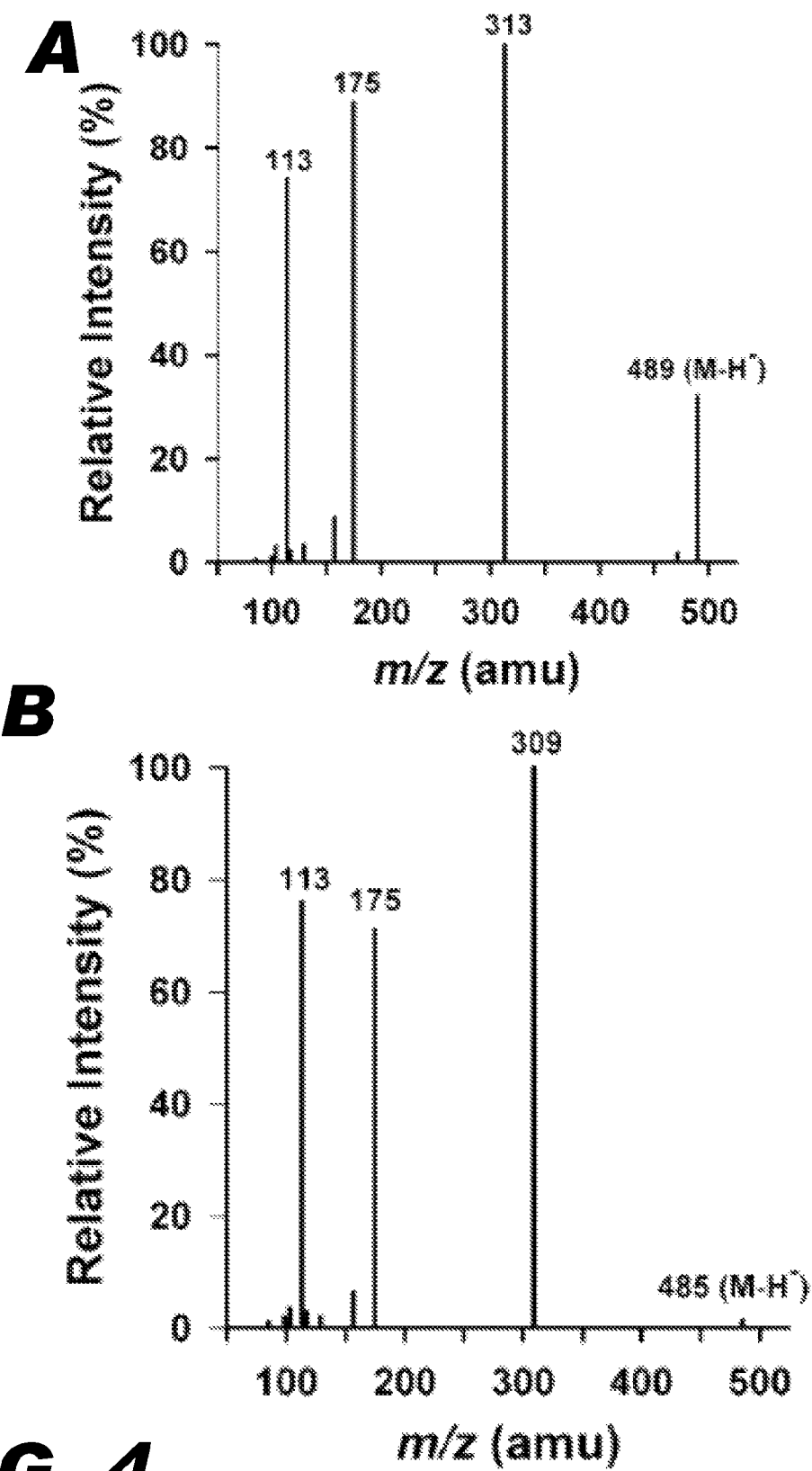
FIG. 4 depicts a series of graphs illustrating MS/MS spectra of the glucuronides of (A) $\Delta^9$-THC, (B) CBN, (C) 11-OH-THC, (D) CBD, and (E) COOH-THC. Spectra are representative of the glucuronidated products shown in FIG. 3. Data were obtained in negative ion mode as described in the Examples.
Figure 4:
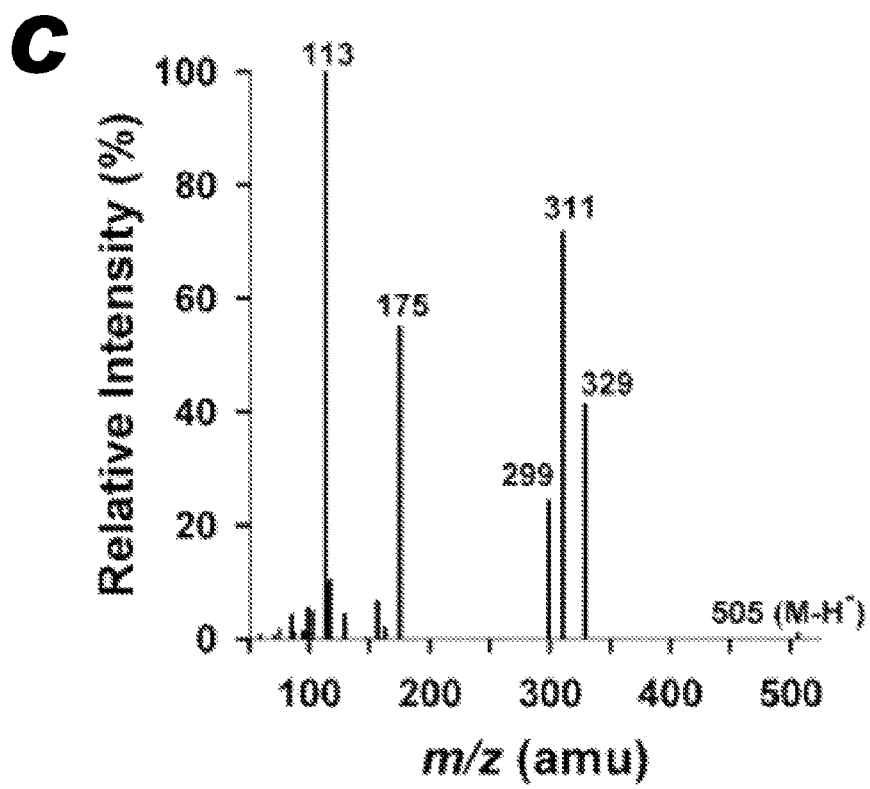
Figure 4:
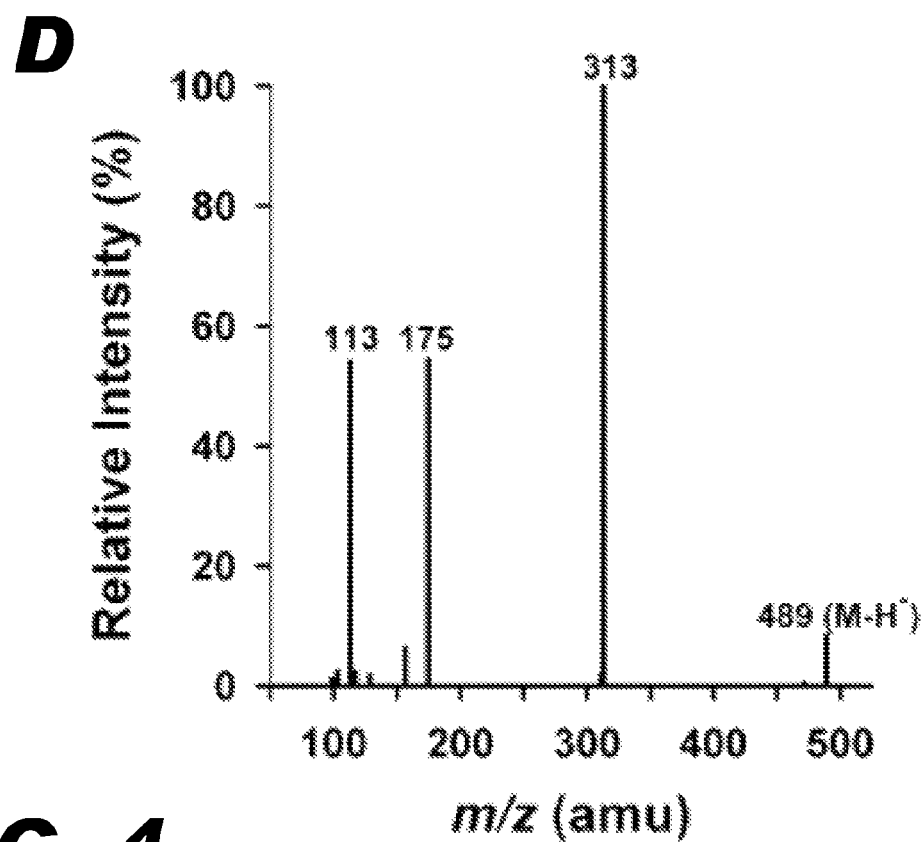
Figure 4E:
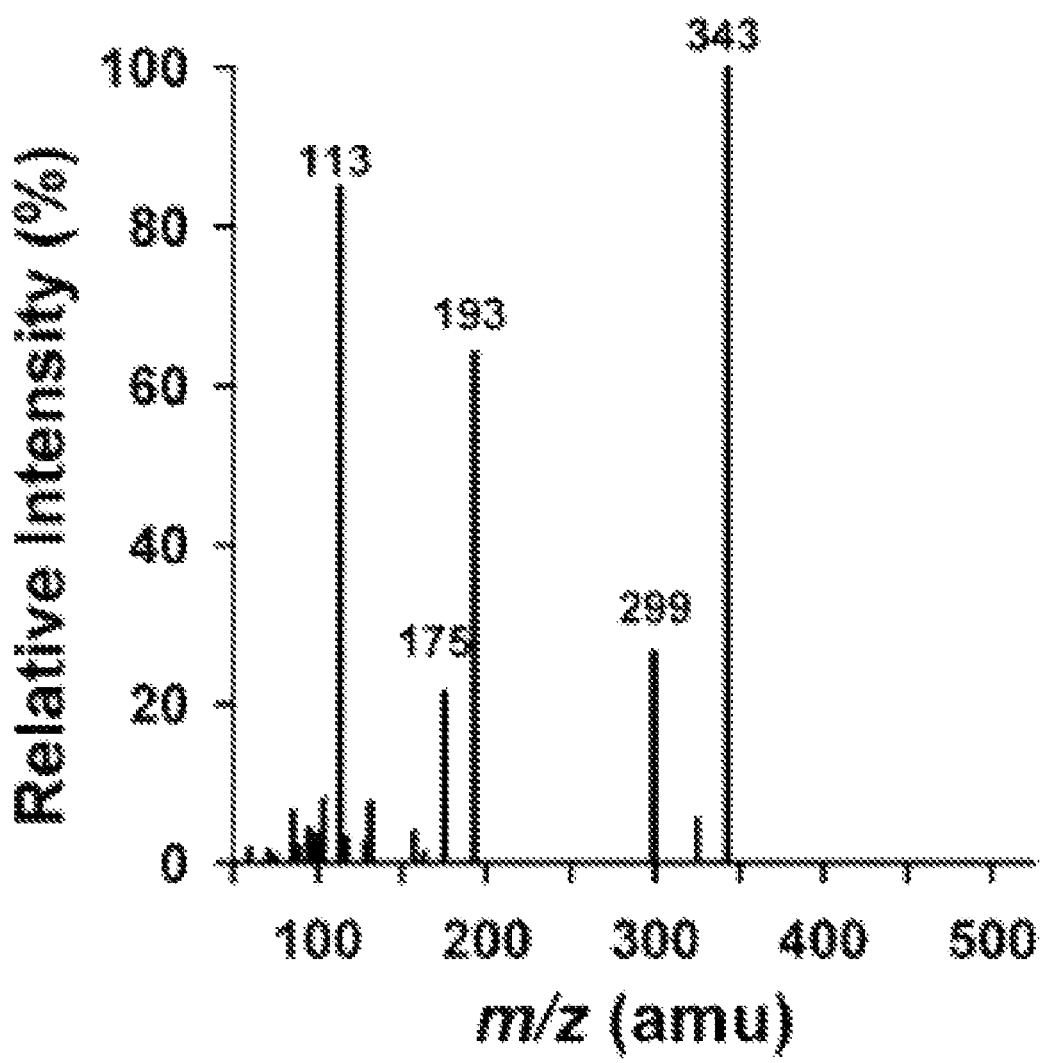
Figure 5:
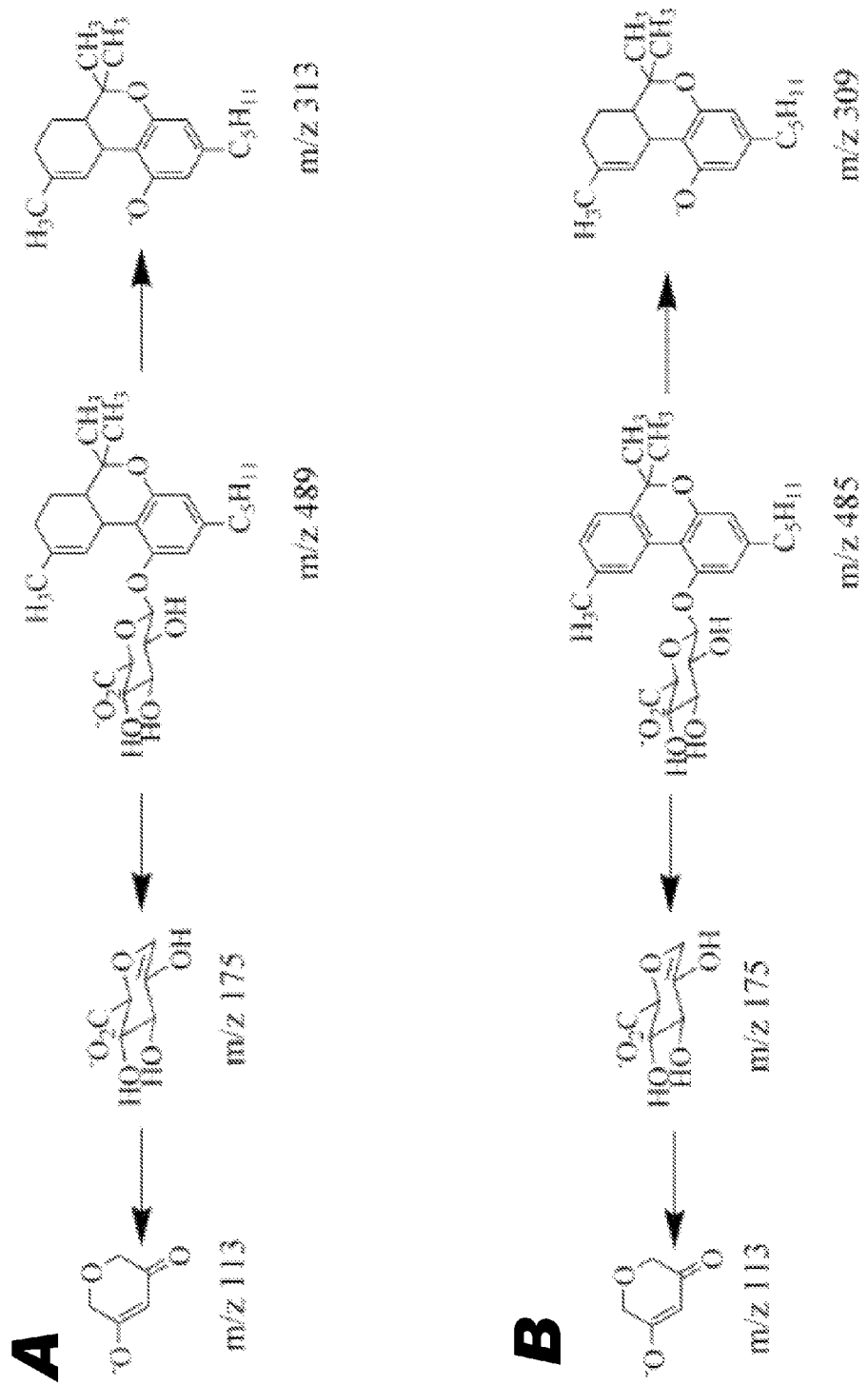
FIG. 5 illustrates proposed MS/MS fragmentation pathways for (A) $\Delta^9$-THC, (B) CBS, (C) 11-OH-THC, (D) CBD, and (E) COOH-THC glucuronides.
Figure 5:
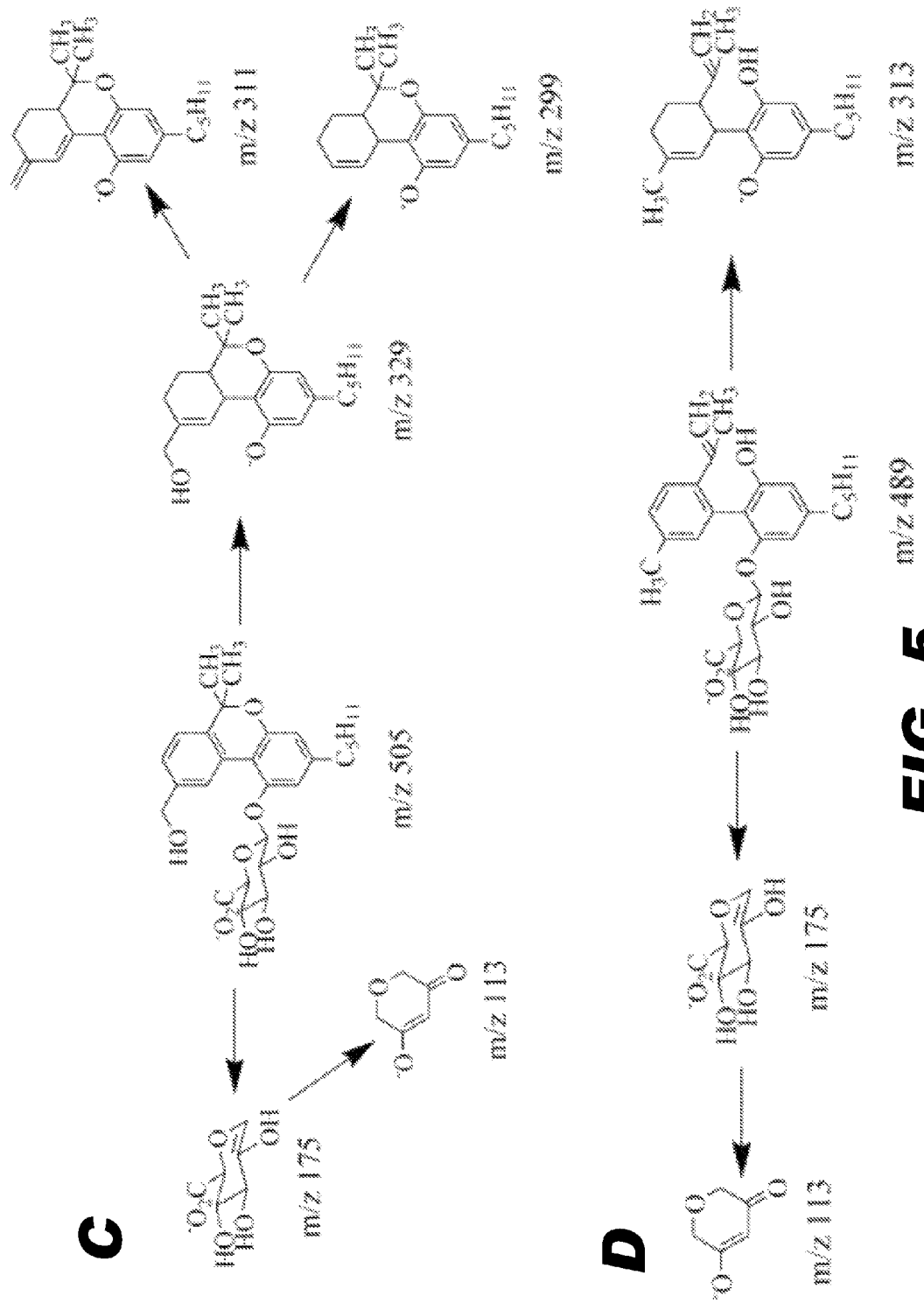
Figure 5E:
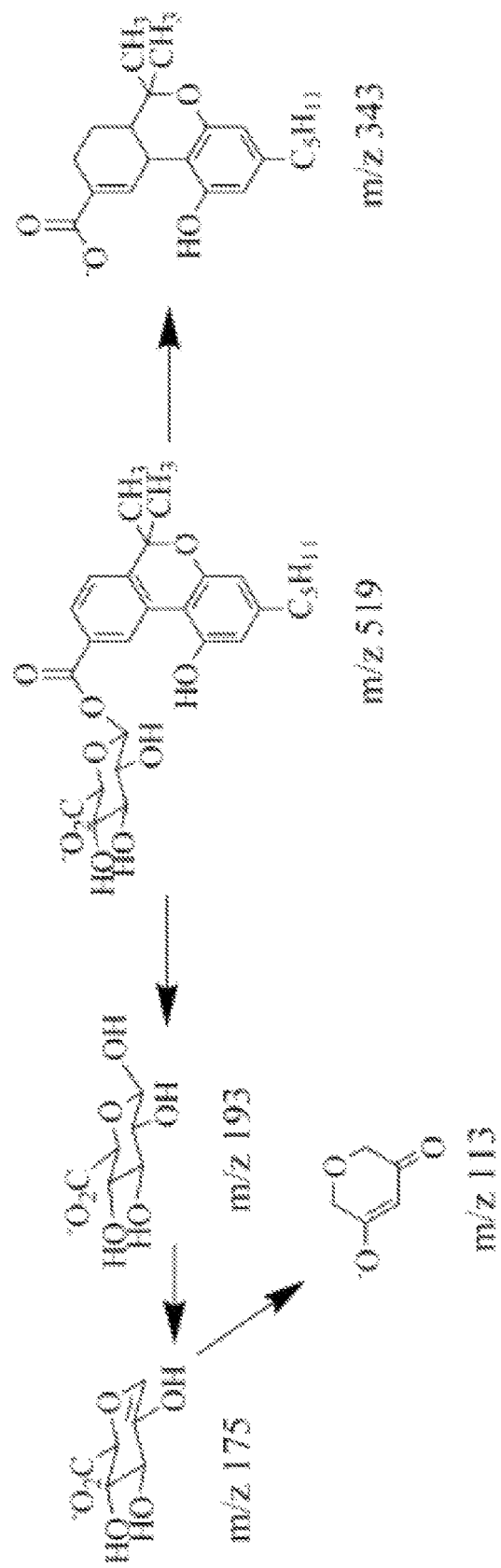
Figure 6:
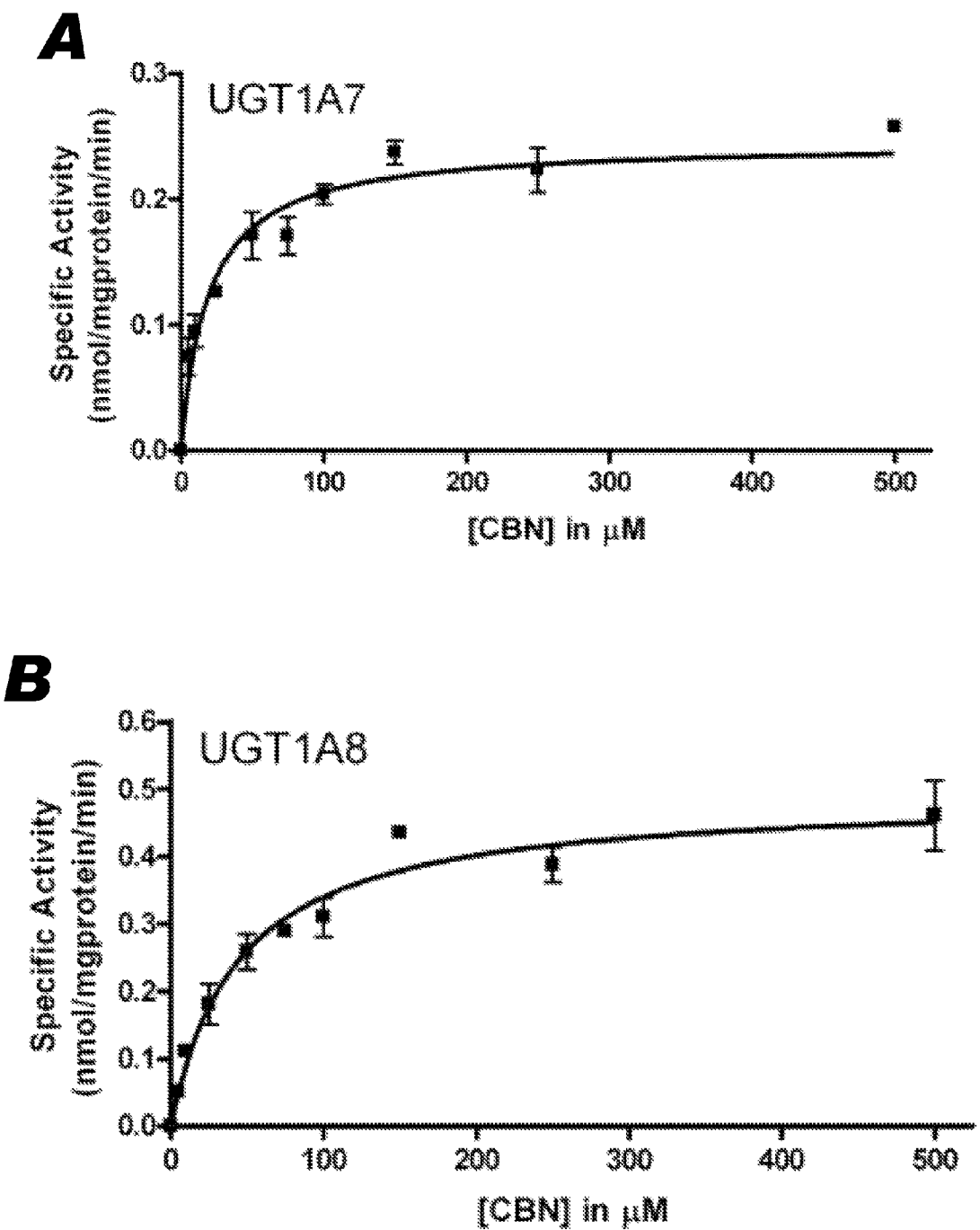
FIG. 6 shows the steady-state glucuronidation of (A-D) CBN, (E-F) 11-OH-THC, and (G-H) COOH-THC with selected recombinant UGT isoforms. Glucuronidation activities of recombinant proteins were measured by incubating membrane fractions containing recombinant UGT1A1O (5 µg) with increasing concentrations (shown in the figure) of substrate at a constant concentration of UDP-GlcUA (4 mM). Curve fits and kinetic constants were determined using GraphPad Prism 4 software and the resulting parameters are included in Table 2.
Figure 6:
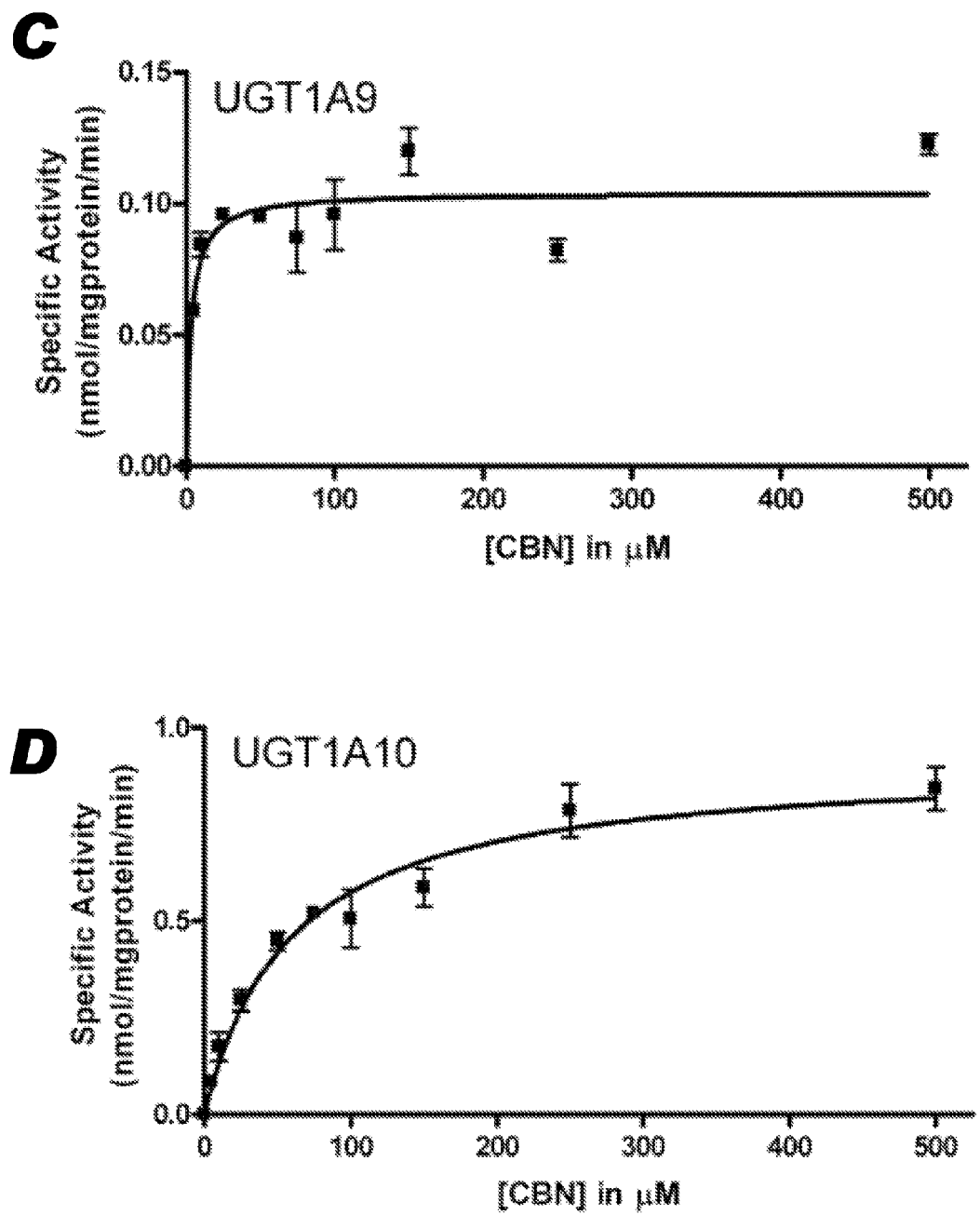
Figure 6:
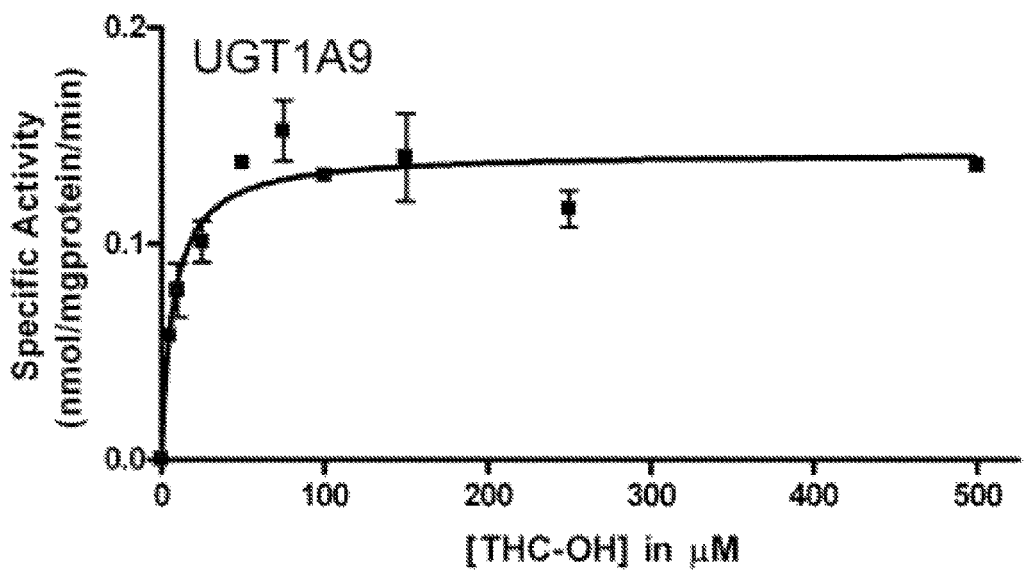
Figure 6:
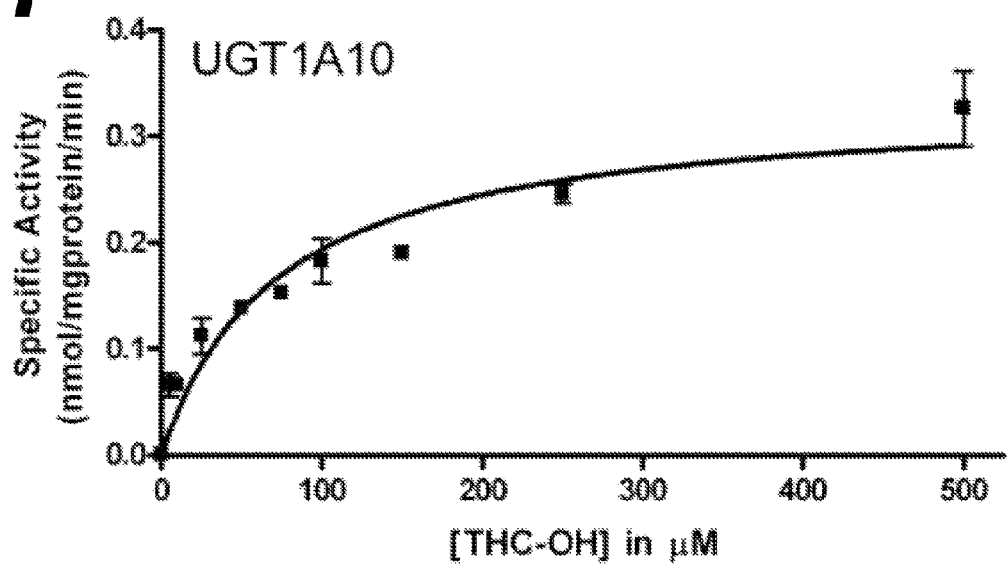
Figure 6:
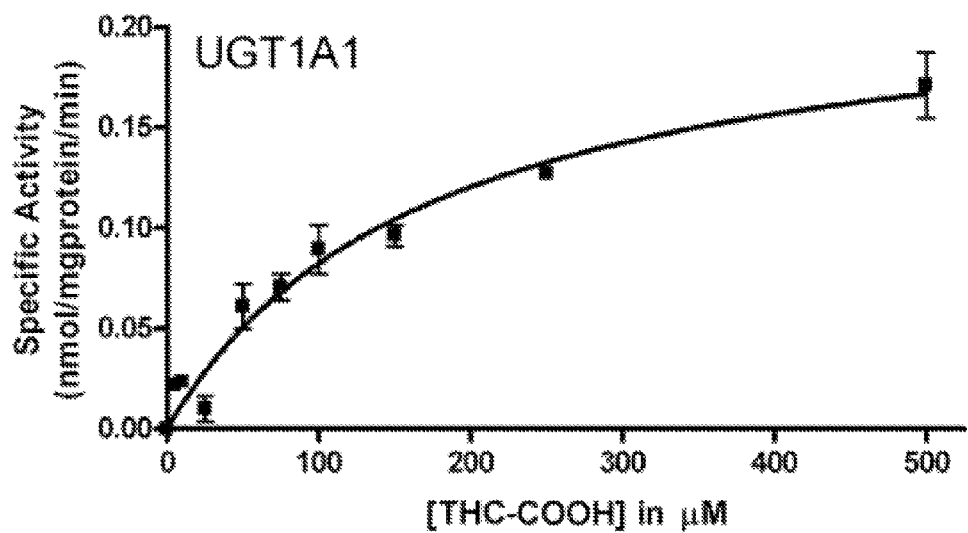
Figure 6:
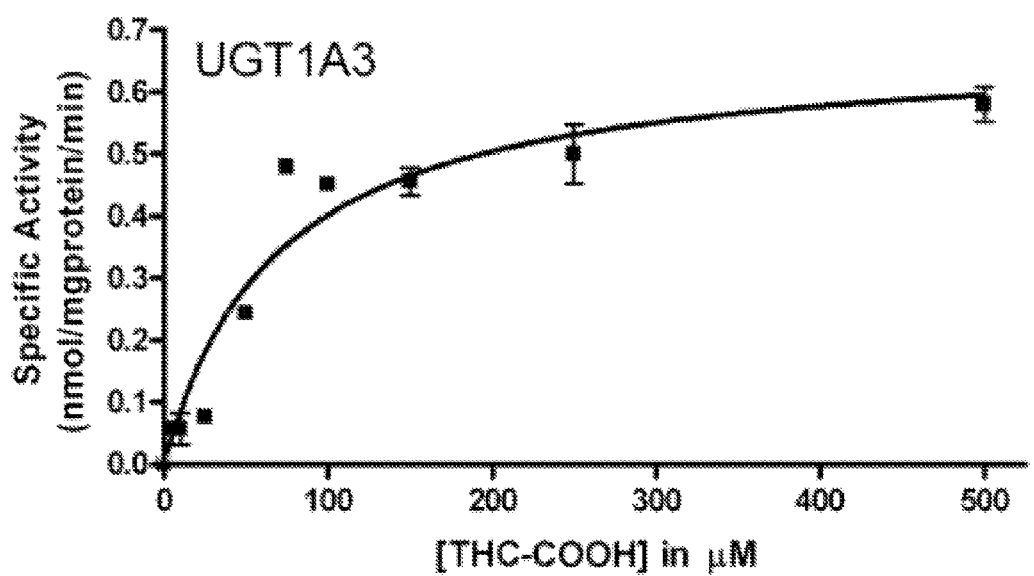

Even though some substrates did not appear to react during the initial screens (FIG. 2), LC-MS/MS confirm that all the tested substrates served as substrates for human UGTs (FIG. 3). Trace amounts of glucuronidated product was detected for all the substrates, but in some cases, where kinetic information could not be obtained, the physiological significance remains to be determined. MS2 chromatographs show predicted glucuronidated metabolites eluting within 2 min (FIG. 3), and the corresponding MS2 spectra have signals consistent with predicted glucuronidated metabolites (FIGS. 4 and 5). The presence of m/z fragments of 313, 309, 343 and 313 in respective reactions suggest the loss of glucuronic acid. Since glucuronidated metabolites demonstrate a propensity to undergo in-source fragmentation during MS/MS analysis, multiple reaction monitoring (MRM) and neutral loss studies were designed to assess whether additional metabolites were formed but not identified during product ion scans. Neither study identified metabolites other than those observed in product ion scans (FIG. 3). In particular, the presence of bis- and/or diglucuronidated products was not detected. MRM studies showed a small degree of in-source fragmentation.

Definite regiochemical assignments can be made for the $(-)$-$\Delta^9$-THC-(C1)-glucuronide, the CBN-(C1)-glucuronide, and the CBD-(C1)-glucuronide. C1 of $(-)$-$\Delta^9$-THC and C1 of CBN are the only active sites which is recognized by UGTs (FIG. 1), CBD contains two hydroxyl groups at the C1 and C5 positions (FIG. 1). However, the C1 and C5 hydroxyl groups are identical due to free rotation about the bond at C6, and since no diglucuronidation was detected, there is only one possible glucuronide product. Although MS/MS data conclusively identified glucuronidated products for 11-OH-THC and COOH-THC, exact regiochemical assignments are complex because multiple reaction sites exist on these substrates and base product ions in mass spectra represent the loss of glucuronic acid. Additional information regarding regiochemistry of glucuronidation can be determined from fragments derived from the glucuronic acid moiety (Wen et al., 2007). Alcoholic and phenolic glucuronides are known to fragment by specific pathways, yielding ions of m/z 175 and 113 for phenolic glucuronides and of m/z 193, 175, and 113 for alcoholic glucuronides. MS2 spectrum of 11-OH-THC glucuronide (FIG. 4) showing the absence of m/z 193 indicates that the site of glucuronidation is on the phenolic OH group. Likewise, the presence of the m/z 193 peak for COOH-THC (FIG. 4) provides supporting evidence for glucuronidation of the carboylate group.

Example 3

Steady-state Kinetics for Cannabinoid Glucuronidation by Recombinant UGTs

Based on our specific activity screen, we subjected selected UGTs to further catalytic studies to determine the respective steady-state parameters for cannabinoid glucuronidation (FIG. 5 and Table 2). Despite MS characterizations confirming the glucuronide production for $(-)$-$\Delta^9$-THC and CBD by UGT1A10 and UGT1A9, the sensitivity of TLC assessments was not adequate to obtain kinetic measurements. We were more successful with other enzymatic reactions. CBN undergoes glucuronidation by four different UGTs with a 17-fold variation in substrate binding. Hepatic UGT1A9 displays the lowest $K_m$ for CBN, while the extrahepatic enzymes, UGT1A7, UGT1A8, and UGT1A10 bound substrate more weakly based on higher $K_m$ values. UGT1A9 and UGT1A10 also glucuronidate 11-OH-THC with affinities similar to those observed for CBN. Despite differences in structures, CBN and 11-OH-THC undergo glucuronidation at similar rates by UGT1A9. By contrast, UGT1A10 was 3-fold more effective at CBN conjugation than 11-OH-THC. Although hepatic UGT1A1 and UGT1A3 demonstrate the only measurable activity toward COOH-THC. these enzymes recognize the substrate more weakly than observed for the other reactions.

TABLE 2

Steady-state parameters for glucuronidation of CBN, 11-OH-THC and COOH-THC by UGT isoforms[a]

| Substrate | UGT isoform[b] | $V_{max}$ (nmol/mg protein/min) | $K_m$ (µM) | $V_{max}/K_m$ (µl/mg protein/min) |
|---|---|---|---|---|
| CBN | UGT1A7 | 0.24 ± 0.01 | 19 ± 3.9 | 12.6 |
| | UGT1A8 | 0.49 ± 0.03 | 44 ± 8.1 | 11.1 |
| | UGT1A9 | 0.10 ± 0.01 | 3.4 ± 1.3 | 29.4 |
| | UGT1A10 | 0.91 ± 0.05 | 59 ± 10 | 15.4 |
| 11-OH-THC | UGT1A9 | 0.14 ± 0.01 | 73 ± 1.9 | 19.2 |
| | UGT1A10 | 0.33 ± 0.03 | 72 ± 19 | 4.58 |
| COOH-THC | UGTIA1 | 0.22 ± 0.02 | 170 ± 37 | 1.29 |
| | UGT1A3 | 0.68 ± 0.06 | 68 ± 17 | 10.0 |

[a]Parameters determined from the fit of initial velocities to a Michaelis-Lenten kinetic scheme using the software GraphPad Prism,
[b]All reactions were normalized as described in Materials and Methods.

Discussion for Examples 1-3

Phase I oxidation and phase II conjugation of $\Delta^9$-THC are generally accepted as important detoxification and excretion processes; however, the impact of these metabolic steps may be more profound than currently appreciated. This study begins characterizing specific human isozymes involved in glucuronidation of classical cannabinoids as well as characterizing products formed during these reactions. This is the first demonstration showing that several cannabinoids serve as substrates for specific human UGTs and HLM and that classical cannabinoid metabolism appears to be tissue specific. LC-MS/MS analysis of product mixtures confirms that glucuronide conjugation does indeed occur for all classical cannabinoids tested. Product ion scans of the desired monoglucuronides provide MS/MS spectra for species with appropriate mass and in most cases allow for specific regiochemistry assignments. $\Delta^9$-THC, CBN, and CBD are all glucuronidated at the C1 position. However, the C5 position is equivalent to C1 in CBD because there is free rotation about the chemical bond localized at the C6 position. Regiochemical assignments for 11-OH-THC and COOH-THC are not as straightforward, because these substrates contain multiple reaction sites that can give rise to different glucuronides. Reactions can occur on the carboxyl terminus of COOH-THC, on the allylic side chain of 11-OH-THC or on the phenolic group which is located in both COON-THC and 11-OH-THC. Structure comparisons as well as substrate recognition studies suggest that glucuronidation is occurring on the carboxyl terminus and on the phenolic hydroxyl group. Analyses of mass spectrum are also consistent with these conclusions (Wen et al., 2007).

The extent of cannabinoid glucuronidation ultimately depends upon structural differences among the compounds. Despite the presence of a hydroxyl group at the C1 position, $\Delta^9$-THC is not readily recognized as a substrate for glucuronidation unless transformed into CBN. This plant-catalyzed process introduces an aromatic ring into the structure of the molecule and subsequently results in the metabolism of this cannabinoid by hepatic UGT1A9 and the extrahepatic UGTs, UGT1A7, UGT1A8. and UGTA10. The recognition of CBN by these UGTs likely involves it stacking with active site phenylalanines, such as those identified in the binding motif for UGT1A10 (Xiang et al. 2006). These enzyme-substrate contacts would favor binding and possibly properly orient the molecule for conjugation. The relative impact of substrate recognition is not uniform among the UGTs. For example, UGT1A9 displays the highest affinity for CBN while UGT1A10 has the lowest.

CYP2C9 oxidation of $\Delta^9$-THC generates 11-OH-THC, a substrate preferentially metabolized by UGT1A9 but also recognized by UGT1A10. It appears that the additional hydroxyl function group in $\Delta^9$-THC provides an alternate site for conjugation and/or alters the binding mode for the cannabinoid to favor UGT catalysis. Further oxidation of 11-OH-THC to COON-THC surprisingly leads to a loss in metabolism by UGT1A9 and UGT1A10, while creating a substrate recognized by hepatic UGT1A1 and UGT1A3. These UGTs must be better suited to tolerate the introduction of a full negative charge to the cannabinoid. The resulting O-esterglucuronide of COON-THC is the main metabolite found in urine (Yamamoto et al. 1987), and thus these hepatic enzymes play a critical role in the metabolic clearance of cannabinoids. Taken together, phase II metabolism of cannabinoids depends on upstream processing, including by enzymes such as CYP2C9 and CYP3A4 (Watanabe et al., 2007).

REFERENCES

1. Barua A B and Olson J A (1987) Chemical synthesis and growth-promoting activity of all-trans-retinyl beta-D-glucuronide. Biochemical Journal 244:231-234.
2. Blaner W S and Olson J A (1994) Retinol and retinoic acid metabolism., in: The Retinoids. Biology, Chemistry, and Medicine. (Sporn M B. Roberts A B and Goodman D S eds). pp 229-255. Raven Press, New York.
3. Brotchie J M (2003) CBI cannabinoid receptor signalling in Parkinson's disease. Current Opinion in Pharmacology 3:54-61.
4. Galiegue S, Mary S. Marchand J. Dussossoy D. Carriere D. Carayon P, Bouaboula M. Shire D. Le Fur O and Casellas P (1995) Expression of central and peripheral cannabinoid receptors in human immune tissues and leukocyte subpopulations. European Journal of Biochemistry 232:54-61.
5. Gallup J M. Barua A B. Fun-H C and Olson J A 1987) Effects of retinoid beta-glueuronides and Nretinoyl amities on the differentiation of HL-60 cells in vitro. Proc Soc Exp Thal !vied 186:269-274.
6. Howlett A C (1995) Pharmacology of cannabinoid receptors. Annual Review of Pharmacology and Toxicology 35:607-634,
7. Iversen L and Chapman V (2002) Cannabinoids: a real prospect for pain relief. Current Opinion in Pharmacology 2:50-55.
8. Janick-Buckner D. Barua A B and Olson J A (1991) Induction of HL-60 cell differentiation by watersoluble and nitrogen-containing conjugates of retinoic acid and retinol. Faseb J 5:320-325.
9. Klein T. Newton C. Larsen K. Lu L. Perkins I, Liang N and Friedman H (2003) The cannabinoid system and immune modulation. Journal of Leukocyte Biology 74:486-496.
10. Kurkeia M. Garcia-ilorsman J A, Luukkanen L, Dorsky S. Taskinen J, Baumann M. Kostiainen R, Hirvonen J and Finel M (2003) Expression and characterization of recombinant human UDPglucuronosyltransferases (UGTs). UGT I A9 is more resistant to detergent inhibition than other UGTs and was purified as an active dimeric enzyme, I Biol Chem 278:3536-3544,
11. Kuuranne T, Kurkela M, Thevis M, Schanzer W, Fine/M and Kostiainen R (2003) Glucuronidation of anabolic androgenic steroids by recombinant human LDP-glueuronosyltransferases. Drug Metab Dispos 31:1117-1124.
12. Little J M, Kurkela M, Sonka J, Jantti S, Kctola R. Bratton S. Finel M and Radorninska-Pandya A (2004) Glucuronidation of oxidized fatty acids and prostaglandins B1 and E2 by human hepatic and recombinant LIDP-alucuronosyltransferases. I Lipid Res 45:1694-1703.
13. Matsuda L, Lolait S, Brownstein M, Young A and Bonner T: (1990) Structure of a cannabinoid receptor and functional expression of the cloned cDNA. Nature 346:561-564.
14. Munro S, Thomas K and Abu-Shaar M (1993) Molecular characterization of a peripheral receptor for cannabinoids. Nature 365:61-65,
15. Racz 1, Bilkei-Gorzo A, Toth Z, Michel K, Palkovits M and Zimmer A (2003) A critical role for the cannabinoid CB 1 receptors in alcohol dependence and stress-stimulated ethanol drinking. Journal of N6Tiroscierice 23; 2453-2458,
16. Radominska-Pyrek A, Zimniak P. Irshaid Y M, Lester R. Tephly T R and St Pyrek J (1987) Glucuronidation of 6 alpha-hydroxy bile acids by human liver microsomes. J clin invest 80:234-241,
17. Ravinet T, Amone M, Delgorge C:, Gonalons N. Keane F. Maffrand J and Soubrie P (2002) Anti-obesity effect of SR 141716, a CBI receptor antagonist; in diet induced obese mice. American Journal of Physiological Regulatory Integrative Comparative Physiology 284; 345-353.
18. Wen Z. Tallman M. Ali S Y and Smith P C (2007) UDP-glucuronosyltransferase 1A1 is the principal enzyme responsible for etoposide glucuronidation in human liver and intestinal microsomes: structural characterization of phenolic and alcoholic Oucuronides of etoposide and estimation of enzyme kinetics. Drug Metab Dispos 35:371-380.
19. Witmer E and Kern S E (2006) Role of morphine's metabolites in analgesia: concepts and controversies. American Association of Pharmaceutical Scientists 8:E348-352.
20. Xiong Y. Bernardi D. Bratton S, Ward M D. Battaglia E, Finel M. Drake R R and Radominska-Pandya A (2006) Phenylalanine 90 and 93 are localized within the phenol binding site of human UDPulucuronosyltransferase 1A10 as determined by photoaftinity labeling, mass spectrometry, and site-directed mutagenesis. Biochemist 45:2322-2332.
21. Yamamoto I. Watanabe K. Kuzuoka K. Narimatsu S and Yoshimura H (1987) The pharmacological activity of cannabinol and its major metabolite, 11-hydroxycannabinol. Chemical and Pharmaceutical Bulletin 35; 2144-2147.

What is claimed is:

1. An isolated classical cannabinoid glucuronide, wherein the classical cannabinoid is selected from the group consisting of CBG, CBC, CBL, CBV, and (±)-11-hydroxy-Δ9-THC (11-OH-THC).

2. A combination of a classical cannabinoid glucuronide and a compound selected from the group consisting of an analgesic, an anti-convulsant, an anti-inflammatory, an anti-anxiety compound, and an anti-emetic compound.

3. A method of detecting a classical cannabinoid glucuronide in a sample, the method comprising liquid chromatography followed by mass spectrometry, wherein the total chromatography run time is less than about eighteen minutes.

4. A combination of a classical cannabinoid glucuronide and a compound selected from the group consisting of an analgesic, an anti-convulsant, an anti-inflammatory, an anti-anxiety compound, and an anti-emetic compound, wherein the classical cannabinoid is selected from the group consisting of CBG, CBC, CBL, CBV, and (±)-11-hydroxy-Δ9-THC (11-OH-THC).

5. A method of detecting a classical cannabinoid glucuronide in a sample, the method comprising liquid chromatography followed by mass spectrometry, wherein the total chromatography run time is less than about eighteen minutes, wherein the classical cannabinoid is selected from the group consisting of CBG, CBC, CBL, CBV, and (±)-11-hydroxy-Δ9-THC (11-OH-THC).

* * * * *